(12) United States Patent
Mai et al.

(10) Patent No.: US 11,020,742 B2
(45) Date of Patent: Jun. 1, 2021

(54) MICROFLUIDIC METERING AND DELIVERY SYSTEM

(71) Applicant: Fitbit, Inc., San Francisco, CA (US)

(72) Inventors: Junyu Mai, Walnut Creek, CA (US); Albert Gutes-Regidor, El Cerrito, CA (US); Rifat Emrah Ozel, San Jose, CA (US); Javier L. Prieto, Oakland, CA (US)

(73) Assignee: Fitbit, Inc., San Francisco, CA (US)

( * ) Notice: Subject to any disclaimer, the term of this patent is extended or adjusted under 35 U.S.C. 154(b) by 180 days.

(21) Appl. No.: 16/414,454

(22) Filed: May 16, 2019

(65) Prior Publication Data

US 2019/0366336 A1 Dec. 5, 2019

Related U.S. Application Data

(63) Continuation of application No. 16/151,062, filed on Oct. 3, 2018, now Pat. No. 10,293,340.
(Continued)

(51) Int. Cl.
*B01L 3/00* (2006.01)
*G01N 33/49* (2006.01)
(Continued)

(52) U.S. Cl.
CPC .......... *B01L 3/502715* (2013.01); *A61B 5/15* (2013.01); *A61B 5/157* (2013.01);
(Continued)

(58) Field of Classification Search
CPC ............... A61B 5/15; A61B 5/150022; A61B 5/150358; A61B 5/157; B01L 2200/026; B01L 2200/027; B01L 2200/0605; B01L 2200/0684; B01L 2200/10; B01L 2200/12; B01L 2300/048; B01L 2300/0681;
(Continued)

(56) References Cited

U.S. PATENT DOCUMENTS

| 3,992,158 A | 11/1976 | Przybylowicz et al. |
| 4,042,335 A | 8/1977 | Clement |

(Continued)

FOREIGN PATENT DOCUMENTS

| EP | 278496 | 8/1988 |
| EP | 303784 | 4/1992 |

(Continued)

OTHER PUBLICATIONS

International Search Report and Written Opinion issued in Application No. PCT /US2018/054401 dated Mar. 22, 2019.
(Continued)

*Primary Examiner* — Jennifer Wecker
(74) *Attorney, Agent, or Firm* — Dority & Manning, P.A.

(57) ABSTRACT

This invention provides devices, systems, and methods for performing point-of-care, analysis, including multiplexed analysis, of a biological fluid analyte, such as blood. The invention includes a cartridge for collecting the biological fluid analyte. The cartridge is configured to be inserted into an assay reader, in which one or more assay reactions may be performed. The assay reader is designed to read and report the results of the one or more assay reactions.

20 Claims, 28 Drawing Sheets

Related U.S. Application Data

(60) Provisional application No. 62/571,178, filed on Oct. 11, 2017.

(51) Int. Cl.
| | | |
|---|---|---|
| *G01N 33/53* | (2006.01) | |
| *G01N 33/00* | (2006.01) | |
| *A61B 5/15* | (2006.01) | |
| *A61B 5/157* | (2006.01) | |
| *G01N 1/00* | (2006.01) | |

(52) U.S. Cl.
CPC .. *A61B 5/150022* (2013.01); *A61B 5/150358* (2013.01); *B01L 3/5023* (2013.01); *B01L 3/502707* (2013.01); *B01L 3/502723* (2013.01); *G01N 1/00* (2013.01); *B01L 2200/026* (2013.01); *B01L 2200/027* (2013.01); *B01L 2200/0605* (2013.01); *B01L 2200/0684* (2013.01); *B01L 2200/10* (2013.01); *B01L 2200/12* (2013.01); *B01L 2300/048* (2013.01); *B01L 2300/165* (2013.01)

(58) Field of Classification Search
CPC ....... B01L 2300/165; B01L 2400/0406; B01L 2400/0457; B01L 3/5023; B01L 3/502707; B01L 3/502715; B01L 3/502723; G01N 1/00
See application file for complete search history.

(56) References Cited

U.S. PATENT DOCUMENTS

| | | | |
|---|---|---|---|
| 4,066,403 A | 1/1978 | Bruschi | |
| 4,144,306 A | 3/1979 | Figueras | |
| 4,152,390 A | 5/1979 | Adamski et al. | |
| 4,472,498 A | 9/1984 | Masuda et al. | |
| 4,587,102 A | 5/1986 | Nagatomo et al. | |
| 4,906,439 A | 3/1990 | Grenner et al. | |
| 4,939,085 A | 7/1990 | Arai et al. | |
| 4,987,085 A | 1/1991 | Allen et al. | |
| 5,008,078 A | 4/1991 | Yaginuma et al. | |
| 5,019,347 A | 5/1991 | Hiratsuka et al. | |
| 5,063,153 A | 11/1991 | Arai et al. | |
| 5,147,606 A | 9/1992 | Charlton et al. | |
| 5,186,894 A | 2/1993 | Katsuyama et al. | |
| 5,215,716 A | 6/1993 | Arai et al. | |
| 5,260,222 A | 11/1993 | Patel | |
| 5,266,460 A | 11/1993 | Sudo et al. | |
| 5,744,096 A | 4/1998 | Jones | |
| 5,939,331 A | 8/1999 | Burd et al. | |
| 6,241,862 B1 | 6/2001 | McAleer et al. | |
| 7,087,397 B2 | 8/2006 | Anaokar et al. | |
| 8,082,810 B2 | 12/2011 | Moles | |
| 8,377,669 B2 | 2/2013 | Campbell et al. | |
| 8,877,142 B2 | 11/2014 | Oehman et al. | |
| 8,900,529 B2 * | 12/2014 | Shaikh | B32B 37/0076 422/503 |
| 2002/0068364 A1 | 6/2002 | Arai et al. | |
| 2003/0146110 A1 | 8/2003 | Karinka et al. | |
| 2004/0067166 A1 | 4/2004 | Karinka et al. | |
| 2004/0265172 A1 | 12/2004 | Pugia et al. | |
| 2005/0130293 A1 | 6/2005 | Blatt et al. | |
| 2005/0183953 A1 | 8/2005 | Su et al. | |
| 2005/0191620 A1 | 9/2005 | McDevitt et al. | |
| 2006/0246600 A1 | 11/2006 | Yang et al. | |
| 2009/0075390 A1 | 3/2009 | Linder et al. | |
| 2014/0138260 A1 * | 5/2014 | Briman | B01L 3/5027 205/775 |

FOREIGN PATENT DOCUMENTS

| | | |
|---|---|---|
| EP | 159727 | 3/1993 |
| EP | 611323 | 8/1994 |
| EP | 298473 | 4/1995 |
| EP | 418235 | 4/1995 |
| EP | 1369473 | 12/2003 |
| EP | 852336 | 4/2004 |
| FR | 2497577 | 7/1982 |
| WO | 2000044930 | 8/2000 |
| WO | 2003072252 | 9/2003 |
| WO | 2005088300 | 9/2005 |
| WO | 2006030579 | 3/2006 |
| WO | 2011137165 | 11/2011 |

OTHER PUBLICATIONS

Extended European Search Report issued in EP Application No. 18865678.9 dated Nov. 13, 2020.
Notice of Allowance issued in U.S. Appl. No. 16/151,062 dated Feb. 6, 2019.
Notice of Allowance issued in U.S. Appl. No. 16/151,062 dated Apr. 8, 2019.

* cited by examiner

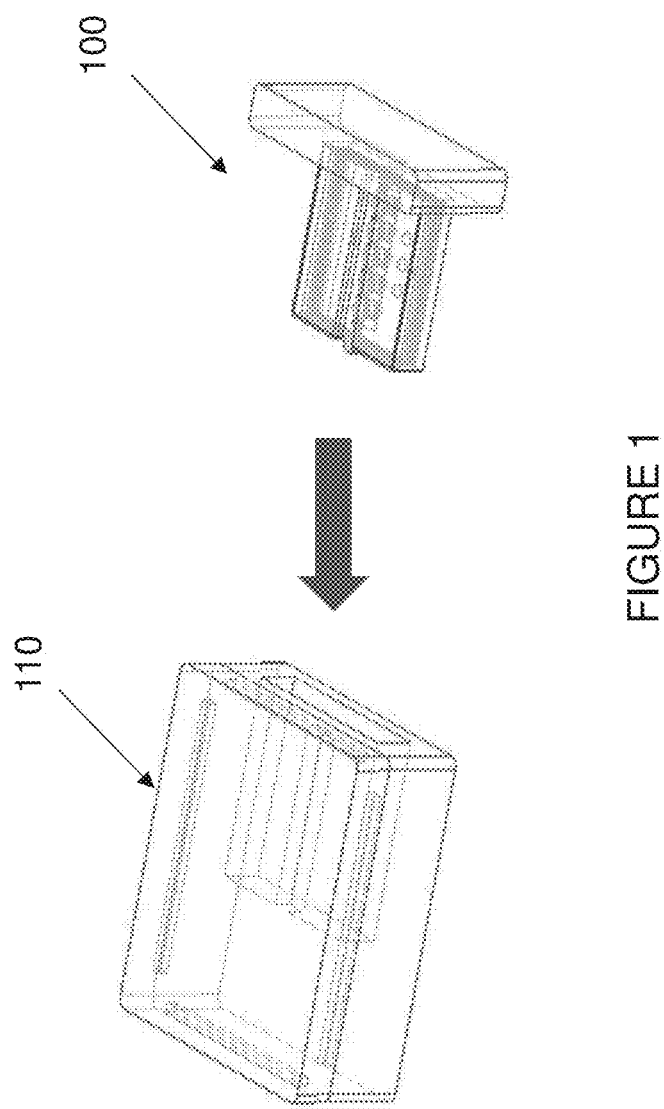

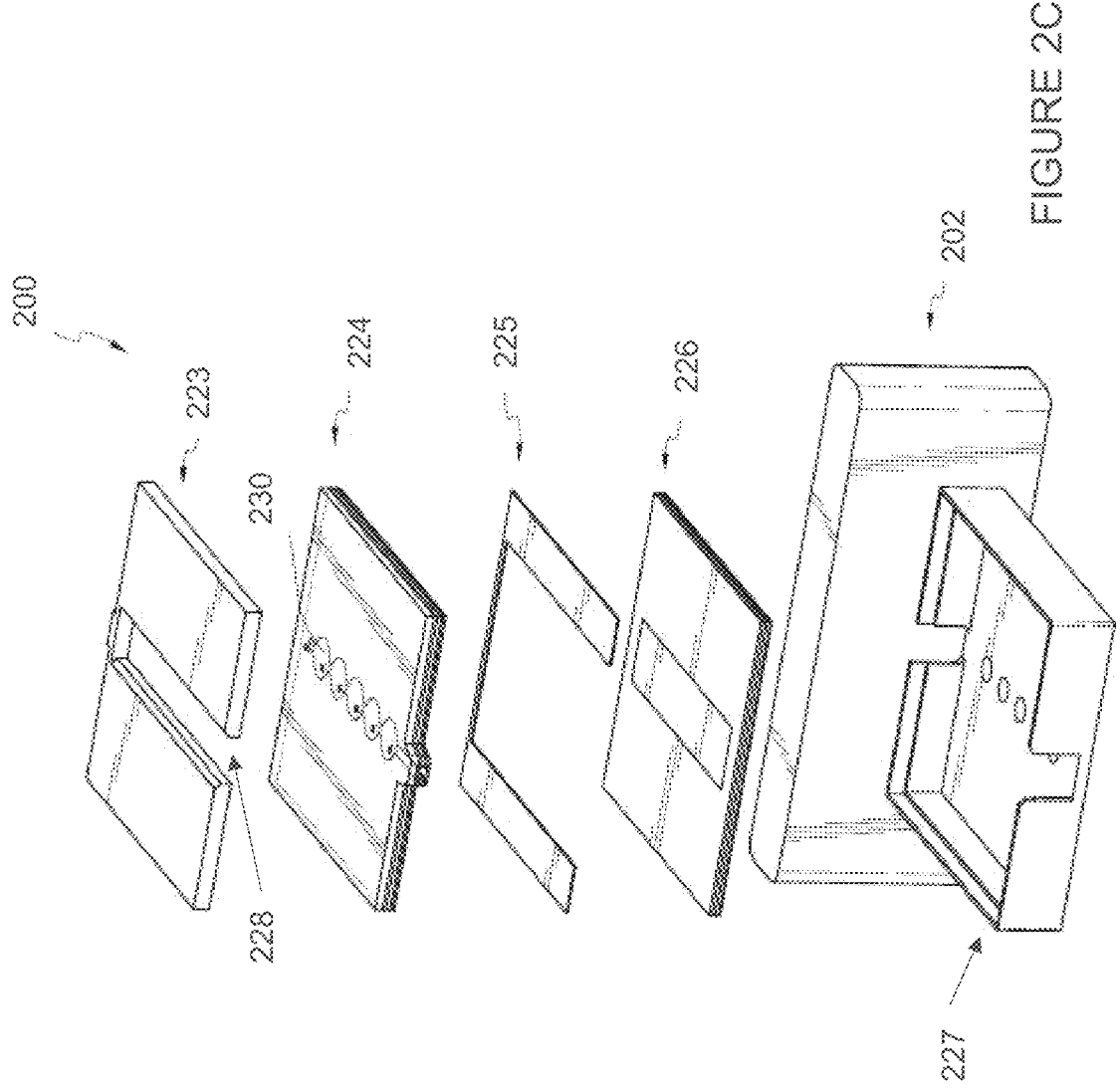

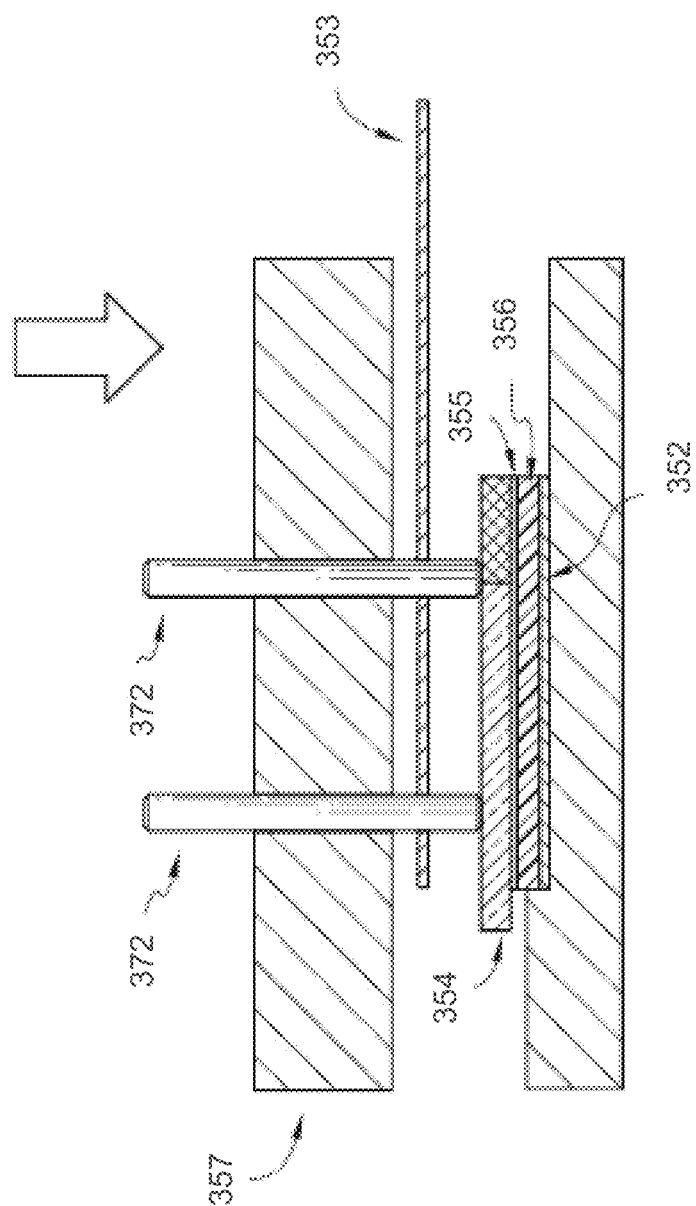

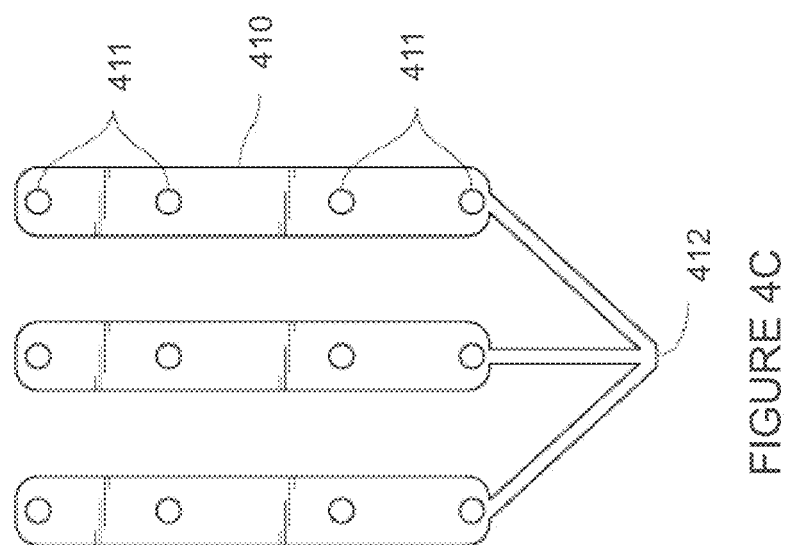

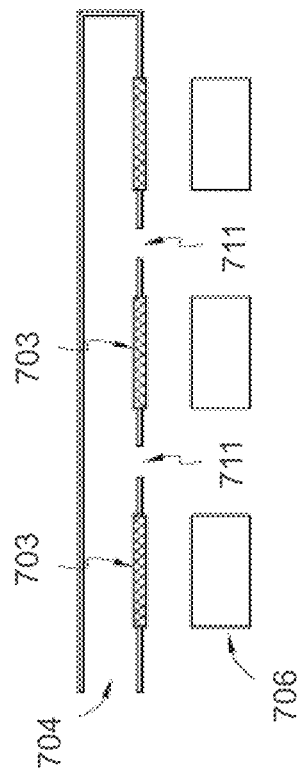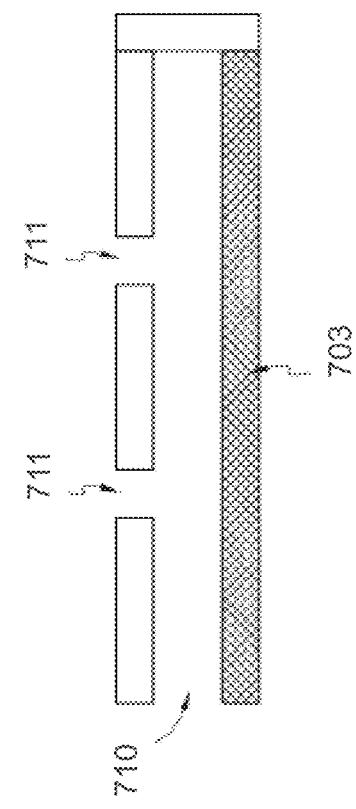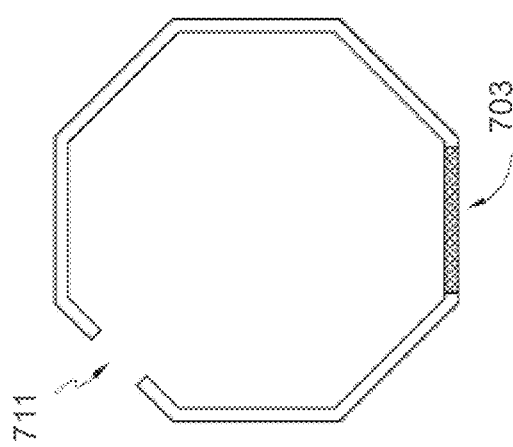

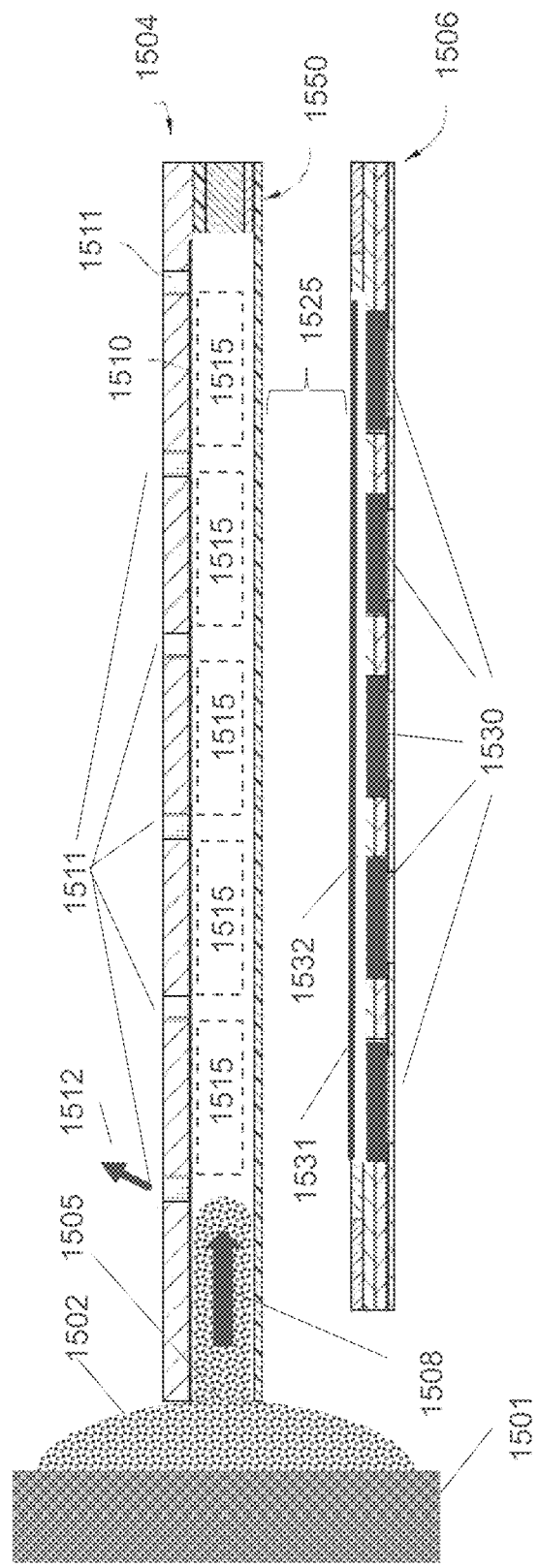
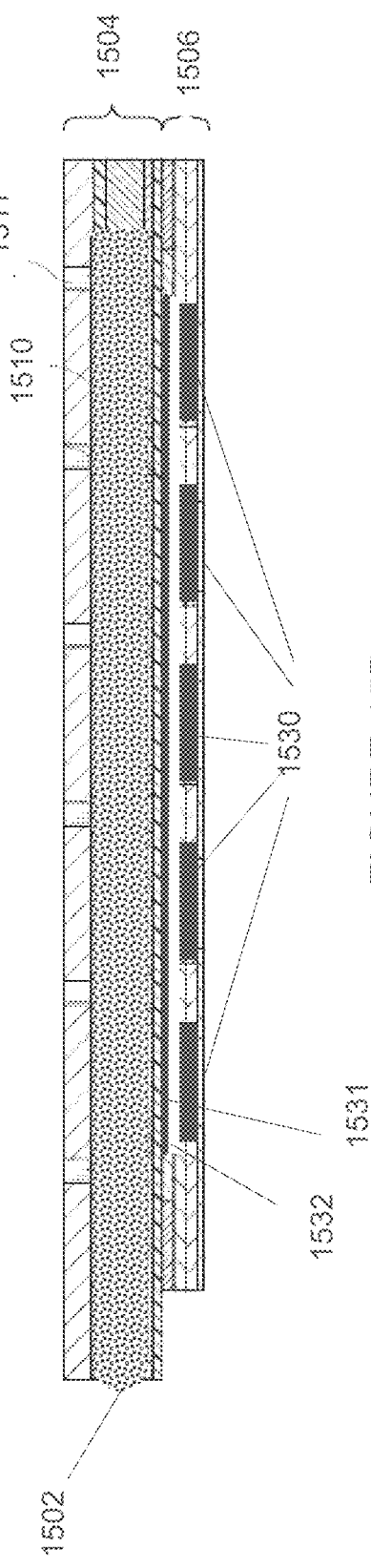
FIGURE 15A
FIGURE 15B

MICROFLUIDIC METERING AND DELIVERY SYSTEM

CROSS REFERENCE TO RELATED APPLICATIONS

This application is a continuation of U.S. application Ser. No. 16/151,062, filed Oct. 3, 2018, which claims the benefit of priority to U.S. Provisional Application No. 62/571,178, filed Oct. 11, 2017, both of which are hereby incorporated by reference in their entirety.

BACKGROUND

Point-of-care (POC) testing refers to performing medical diagnostic tests at the time and place ("point of care") that the patient is being treated. Point-of-care testing is advantageous over traditional diagnostic testing where patient samples are sent out to a laboratory for further analysis, because the results of traditional diagnostic tests may not be available for hours, if not days or weeks, making it difficult for a caregiver to assess the proper course of treatment in the interim.

Although some POC testing devices are available, they typically suffer from one or more serious drawbacks. For example, many POC testing devices can analyze only one target analyte at a time. And while some POC testing devices can perform multiplexed analysis, e.g., by testing multiple analyte targets in one test cartridge, such POC devices typically suffer from serious drawbacks, such as the inability to precisely control the volume of blood sample dispensed for each analysis, which adversely affects the accuracy of the POC testing.

Designing POC testing devices for in-home is particularly challenging, because such devices are often operated by people with limited training or no training at all. Current systems can often require the user to follow multiple steps of operations of multiple separated parts (pipettes, test strips, etc.). User-introduced errors can easily cause inaccurate or failed assays. To avoid user-introduced errors, current POC devices separate sample collection, sample preparation, and the assay to avoid common problems such as timing inconsistencies, inaccurate sample volume, air bubble formation, and other issues. However, this approach presents other challenges. For example, sample collection is often done using plastic pipettes or glass capillaries that need to be filled up to a given mark. Accuracy of an assay depends on the accuracy of a sample volume, which in turn relies on relies on a user's ability to consistently and accurately fill a capillary or pipette to collect the appropriate sample volume. One of the biggest problems relating to accurate sample collection is the creation of undesirable air bubbles during the collection process. It can be difficult to fill the capillary in a single motion, and thus users often use several stop-and-fill motions, which may temporarily leave the tip of the capillary exposed to air rather than the desired fluid analyte (e.g., blood). When this happens, air bubbles can then get into the capillary or pipette and prevent the collection of the appropriate volume of fluid analyte, thereby introducing errors in the sample volume.

In addition to problems associated with inaccurate sample volume collection, additional problems may arise when conducting the assay or assays associated with a conventional POC testing system. For example, after a sample is collected, POC systems can require the user to manually dispense the blood sample from the pipet or capillary to the cartridge that can perform the assay. In this step, additional user-introduced error such as mis-aiming, touching the assay pad, or incomplete or prolonged dispensing can further adversely affect the accuracy assay results. For instance, in most point-of-care (POC) testing systems for blood samples, certain sample preparation steps need to be performed prior to a final chemical reaction that provides the test result. These sample preparation steps may include complex preparation steps such as plasma separation, cell lysis, or others, depending on the assay. The time required to complete such complex preparation steps may be comparable to the time required for blood to undergo undesirable clotting, which further introduces error into the assay results. Thus, it would be desirable to have a POC system that precisely controls the amount of analyte that is collected, minimizes the analyte collection time to avoid undesirable side reactions (e.g., blood clotting); and controls the dispensing time during which the target analyte undergoes chemical reactions with the assay chemicals to provide an assay result.

BRIEF DESCRIPTION OF THE DRAWINGS

Embodiments of the present disclosure will now be described hereinafter, by way of example only, with reference to the accompanying drawings in which:

FIG. 1 provides a schematic drawing of a system comprising a cartridge and a reader according to one embodiment of the invention;

FIG. 2A-2C illustrates an embodiment of the cartridge of the microfluidic device;

FIG. 3C-3D illustrate an embodiment using moving pins to compress the metering stack and assay stack when the cartridge is inserted into an assay reader;

FIG. 7A-7C illustrate embodiments of channels with various positions of venting holes;

FIG. 15A-D provides a schematic illustration of the operation of a cartridge according to some embodiments of the invention;

DETAILED DESCRIPTION

Figure 2B:
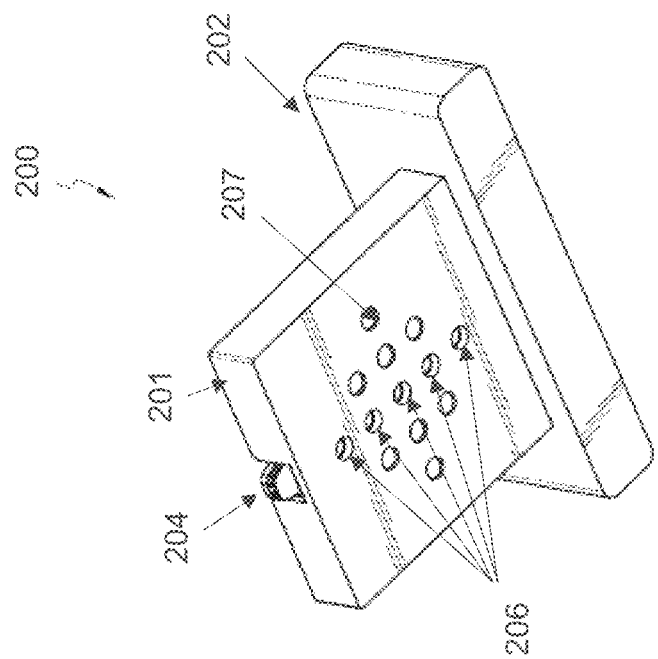

This invention relates to a microfluidic device for rapid point-of-care collection of a fluid analyte and multiplex analysis thereof. This invention also provides methods and systems for using a microfluidic device to provide rapid multiplexed analysis of a fluid analyte. The present disclosure generally provides methods for a microfluidic device for sample collection and testing. Some of the devices described herein comprise a sample collection cartridge. The sample collection cartridge can be used in combination with an assay reader for point-of-care (POC) diagnostics as described herein.

One aspect of this invention is to provide a cartridge for collecting a target analyte for testing. The cartridge includes a metering stack configured to receive and distribute a target analyte along a first channel. The first channel has a bottom that includes a porous or mesh material and one or more venting holes located along the first channel. The cartridge further includes an assay stack comprising at least one assay component that includes one or more assay pad. Each assay pad comprises a reagent for performing an assay on the target analyte or a portion thereof. The cartridge also includes a spacer layer disposed between the metering stack and the assay stack. The spacer layer provides a gap between the metering stack and the assay stack that prevents the target analyte from flowing from the metering stack into the assay stack when the cartridge is in an uncompressed state. The porous or mesh material permits the target analyte to flow from the metering stack to the assay stack only when the cartridge is sufficiently compressed to bring the metering stack in contact with the assay stack.

Another aspect of this invention is to provide an assay reader. The assay reader includes a chamber configured to receive a cartridge. The assay reader also features a compression mechanism configured to compress the cartridge when or after the cartridge is inserted into the chamber after collection of a target analyte. This causes one or more assay reactions to start within the cartridge. The assay reader also includes a detection system for measuring a signal change corresponding to the one or more assay reactions.

The invention also provides a system for multiplexed analysis of a target analyte. The system comprises a cartridge which includes a metering stack configured to receive and distribute the target analyte along a first channel. The first channel has a bottom that comprises a porous or mesh material. The system also includes an assay stack comprising at least one assay component. Each assay component includes one or more assay pads that contain a reagent for performing an assay on the target analyte or a portion thereof. The cartridge in the system further includes a spacer layer disposed between the metering stack and the assay stack. The spacer layer provides a gap between the metering stack and the assay stack that prevents the target analyte from flowing from the metering stack into the assay stack when the cartridge is in an uncompressed state. In addition, the porous or mesh material permits the target analyte to flow from the metering stack to the assay stack only when the cartridge is sufficiently compressed to bring the metering stack in contact with the assay stack. The system further includes an assay reader that includes a chamber configured to receive the cartridge and a compression mechanism configured to compress the cartridge when or after the cartridge is inserted into the chamber after collection of the target analyte. This causes one or more assay reactions to start at the same time within the cartridge. The system further includes a detection system for detecting a signal change corresponding to the one or more assay reactions.

In yet another aspect, the invention provides a method of performing a plurality of assays. The method includes receiving a target analyte into a first channel in a cartridge, and inserting the cartridge into an assay reader, thereby compressing the cartridge to expose at least one component of the target analyte stored in a first channel to one or more assay pads. This causes the assay reactions to start. The method also includes the step of detecting one or more signal changes associated with the one or more assay reactions.

The invention also provides a method of fabricating a cartridge. The method comprises obtaining a first layer comprising (1) a layer of polymeric material with a channel formed therein, wherein the channel comprises at least one venting hole disposed along the channel, (2) a porous or mesh material attached on a bottom surface of the polymeric material such that the channel is bounded on a bottom surface by the porous or mesh material. The method also comprises the steps of obtaining a second layer comprising one or more assay pads, each comprising a porous material capable of absorbing analyte from the bottom of the channel, and a reagent for performing an assay on the target analyte or a portion thereof. The method also includes the steps of obtaining a compressible intermediate layer and combining the first layer, compressible intermediate layer, and second layer in a cartridge housing such that the compressible intermediate layer separates the first layer and the second layer when the compressible intermediate layer is in an uncompressed state, and the channel is aligned with the one or more assay pads in a direction perpendicular to the first layer.

The invention also provides a method of fabricating a cartridge that comprises combining a first layer, a compressible intermediate layer, and a second layer in a cartridge housing. The first layer comprises (1) a layer of polymeric material with a channel formed therein and (2) a porous or mesh material attached on a bottom surface of the polymeric material such that the channel is bounded on a bottom surface by the porous or mesh material. The second layer comprises one or more assay pads, each comprising a reagent for performing an assay on the target analyte or a portion thereof. The compressible intermediate layer comprises a compressible material that separates the first layer and the second layer when the compressible intermediate layer is in an uncompressed state. When the first layer, compressible intermediate layer, and second layer are stacked in the cartridge housing, the channel is aligned with the one or more assay pads in a direction perpendicular to the first layer.

Any of the features, components, or details of any of the arrangements or embodiments disclosed in this application, including without limitation any of the cartridge embodiments and any of the testing or assay embodiments disclosed below, are interchangeably combinable with any other features, components, or details of any of the arrangements or embodiments disclosed herein to form new arrangements and embodiments.

In one aspect, this invention provides an easy-to-use and fully integrated POC testing device that allowed for multiplexed analysis of a target analyte. As described herein, the POC testing device simplifies target analyte sample collection and obviates problems associated with conventional POC testing devices, including unwanted bubble formation, inaccuracy in collected sample volumes, and uncertainty in target analyte dispensing time when the assay is conducted. In addition, the POC testing devices according to the invention contain few moving parts and do not employ mechanical devices, such as plungers or valves, for collecting the target analyte samples. In this way, the POC testing devices of the invention are more mechanically robust and minimize the chance for user errors.

FIG. 1 shows a POC testing device according to one exemplary embodiment of the invention. The POC testing device comprises a cartridge 100 and an assay reader 110. As described herein, cartridge 100 is used to collect the target analyte. The collection process also distributes the target analyte within cartridge 100. After the target analyte is collected in cartridge 100, the user inserts cartridge 100 into assay reader 110. As described herein, the act of inserting cartridge 100 into assay reader 110 results in the compression of cartridge 100, thereby causing at least one component of the target analyte to be distributed to a plurality of assay pads. In this way, the act of inserting cartridge 100 into assay reader 100 commences a plurality of assay reactions that provide information regarding the contents of the target analyte. As described herein, assay reader 110 is equipped with a detection system that is used to detect the results of the assay reactions that occur at the assay pads of cartridge 100. The detection system is not particularly limited and may be a detection system which causes a measurable signal change as the result of an assay reaction. Non-limiting examples of suitable detection systems include optical and electrochemical detection systems as described herein.

Figure 2A:
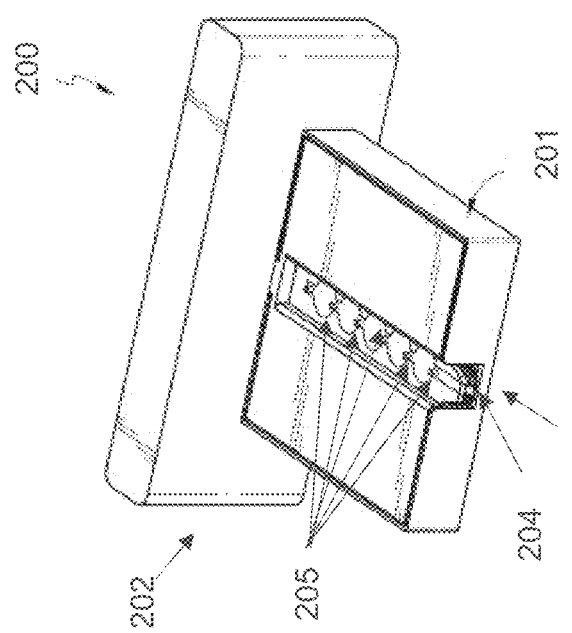

FIG. 2A illustrates a top view of an embodiment of a cartridge 200. In FIG. 2A, cartridge 200 includes a housing 201 attached to a handle 202. In general, cartridge 200 is designed to be easy to handle by the user and to provide a protective shell for the microfluidic distribution system and assay components housed within cartridge 200. In general, suitable materials for housing 201 and handle 202 include polyolefinic compounds, such as polyethylene, polypropylene, and other polymeric resins or compounds that are amenable to sterilization procedures known in the medical device manufacturing art, e.g., exposure to ethylene oxide gas. During sample collection, cartridge 200 is brought into contact with a target analyte (e.g., blood). The target analyte is drawn into channel 203 and via channel opening 204 by capillary action. In some embodiments, channel 203 comprises a plurality of receiving chambers located along channel 203. In preferred embodiments, each receiving chamber is positioned between two venting holes, which facilitate the division of the target analyte in the channel into multiple aliquots which flow to the assay pads in the assay stack. It should be recognized that the channel opening 204 can function as a venting hole and that neighboring receiving chambers can share a common venting hole between them. The venting holes, in combination with the porous or mesh material described herein, prevent unwanted bubble formation as the target analyte is drawn into the receiving chambers. FIG. 2B illustrates a bottom view of an embodiment of the cartridge 200. In FIG. 2B, the bottom portion of housing 201 comprises a plurality of assay detection ports 206 aligned with channel opening 204. The assay detection ports 206 permit the assay results to be interrogated, for example, by optical detection methods as described herein. In addition, the bottom portion of housing 201 may comprise plurality of holes 207, which are additional assay detection ports that may be used with assay components and microfluidic channels that are arranged in a corresponding configuration.

FIG. 2C provides an exploded view of the components of the cartridge 200, according to one embodiment of the invention. In FIG. 2C, the outer shell of cartridge 200 comprises a handle 202, bottom housing portion 227, and a cap 223 that is equipped with a slot 228. The bottom housing portion 227 can be a cuboid shape enclosure with one open side. The enclosure shape of the bottom housing portion 227 protects the components within the interior chamber and can avoid accidental actuation of the device. The cap 223 can fit to the open side of the bottom housing portion 227 and have a shape and size that corresponds to the open side of the bottom housing portion 227. When the bottom housing portion 227 and cap 223 of the housing are assembled together, an interior chamber can be formed for enclosing other components of the cartridge within the interior chamber. In other embodiments, the cap 223 and bottom housing portion 227 do not form an enclosure with an interior chamber and can be rigid structures positioned on the top of a metering stack and bottom of an assay stack, which are described herein.

In preferred embodiments, bottom housing portion 227 and cap 223 can be formed of a material to provide a rigid structure to the cartridge 200. For example, the bottom housing portion 227 and the cap 223 can be a plastic material, as described herein. The bottom housing portion 227 and cap 223 can be moveable or non-moveable with relation to each other. In preferred embodiments, when cartridge 200 is inserted into an assay reader, the components within the interior chamber are compressed to cause at least one portion of the collected target analyte to be delivered to a plurality of assay components.

In some embodiments, the cartridge does not comprise a cap and bottom housing portion. In such embodiments, the cartridge does not include the housing 201 (see FIG. 2A) and the metering stack and assay stack can be inserted into an assay reader without an enclosure around it.

As shown in FIG. 2C, cartridge 200 can include a metering stack 224, a spacer material 225, and an assay stack 226. The metering stack 224 can be used to collect a sample of the target analyte (e.g., blood) and the assay stack 226 comprises assay components necessary for the test to be carried out as discussed in detail herein. As used herein, the term "metering" refers to collecting a liquid sample of a target analyte and delivering one or more predetermined volumes of at least a portion of the target analyte to the assay components for further analysis via the assay components contained in the assay stack. When assembled into a cartridge, the metering stack 224, a spacer material 225, and an assay stack 226 can arranged in a stack.

The spacer material 225 is a compressible layer that may be positioned between the metering stack 224 and assay stack 226 as shown in FIG. 2C. In an embodiment, the spacer layer 225 may be a flexible material that can be compressed in the vertical direction when the cartridge is inserted into the assay reader and the metering stack 224 is moved into contact with or close proximity to the assay stack 226. In some embodiments, the spacer layer 225 can be a flexible material, such as foam, rubber, porous polymer, metal, cotton, or other bending, folding, or moving mechanisms such as a clamp or spring. In some embodiments, the metering and assay stacks are initially separated by an air gap maintained by the spacer layer 225. In certain embodiments, spacer material 225 is physically affixed to another layer, such as metering stack 224 or assay stack 226 before the layers of the cartridge are brought together. Typically, the metering and assay stacks remain separated throughout the sample collection process. In such embodiments, the separation between the metering stack and the assay stack prevent a chemical reaction from starting during the target analyte collection step. When the spacer material 225 is compressed, the metering stack 224 and assay stack 226 can come into contact with or brought into close proximity to each other.

In preferred embodiments, when the metering stack is fully filled with the target analyte, the cartridge is inserted into an assay reader. Preferably, the material that is used for the top surface of channel 230 is sufficiently transparent so that a user can determine by visual inspection when the channel 230 is filled and the cartridge is ready for insertion into the assay reader. The assay reader is configured to accept the assay reader and comprises a mechanism that compresses the spacer layer, thereby pushing the metering stack and assay stack together when the cartridge is inserted into the assay reader. The compression of the spacer layer causes a predetermined volume of at least a portion of the collected target analyte to flow to assay components in the assay stack. In this way, the act of compressing the metering and assay stacks together can, in certain embodiments, provide a well-defined point in time that marks the start of the assays of the assay components in the assay stack.

Figure 3A:
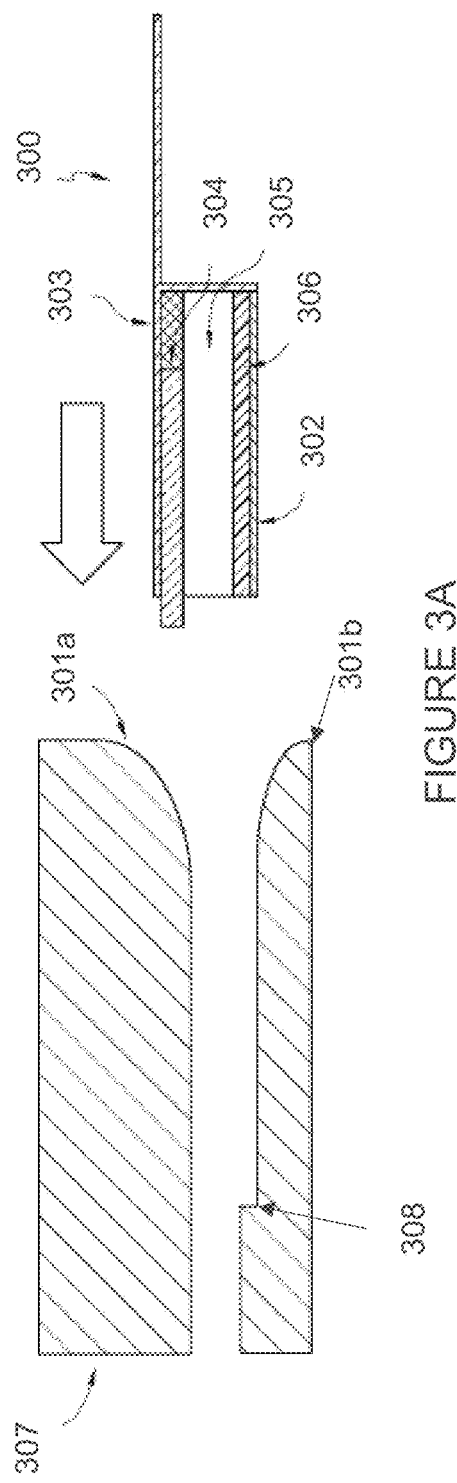
FIG. 3A-3B illustrate an embodiment of a physical compression of the metering stack and assay stack when the cartridge is inserted into an assay reader.
Figure 3B:
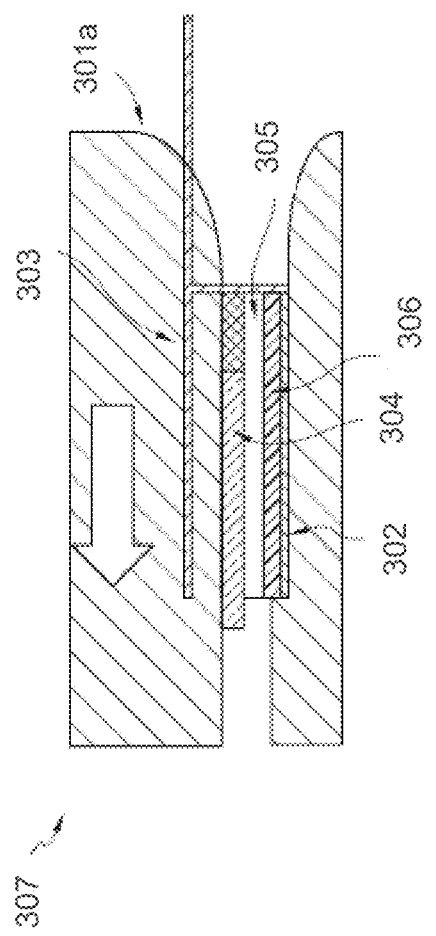

In some embodiments, the metering stack and assay stack can be pushed together inside the assay reader by non-movable physical constraints as illustrated in FIGS. 3A-B. FIGS. 3A-B illustrate an embodiment in which physical compression of the metering stack 304 and assay stack 306 occurs when cartridge 300 is inserted into an assay reader 307. FIG. 3A illustrates the cartridge 300 and assay reader 307 before the cartridge 300 is inserted into the assay reader 307 in the direction indicated the arrow in FIG. 3A. FIG. 3B illustrates the cartridge 300 after it has been inserted into a slot of the assay reader 307. The positioning of a top portion 301a of the assay reader slot with respect to a bottom portion 301b of the slot causes the metering stack 304 to move vertically within the cartridge 300, thereby compressing the spacer material 305. If desired, the top portion 301a may be sized to compress only the portion of the metering stack that is directly above the assay components in the assay stack. This may be achieved, for example, by sizing the top portion 301a such that it slides into a slot in the cap 303 of the cartridge (e.g., slot 228 in FIG. 2C). If desired, the assay reader slot may be shaped to limit the degree to which cartridge 300 may be inserted into the assay reader 307. For example, once bottom housing portion 302 is fully inserted, it may interact with lip 308 to prevent further insertion of cartridge 300 into assay reader 307. Once the spacer material 305 is compressed from the insertion of cartridge 300 into assay reader 307, the collected target analyte flows from the metering stack 304 to the assay components in the assay stack 306.

Alternatively, the metering stack 304 and assay stack 306 can be pushed together by one or more moving parts in the assay reader, non-limiting examples of which include pushing pins, or movable blocks actuated by a motor, servo, air pressure, magnetic force, electro-magnetic force, manual force exerted by the user, or other moving mechanisms. Combinations of these mechanisms are also expressly contemplated by the invention. In some embodiments, the metering stack 304 and assay stack 306 can be pushed together by one or more moving parts in the assay reader such as a plunger pressor using electromechanical forces in the assay reader.

Figure 3C:
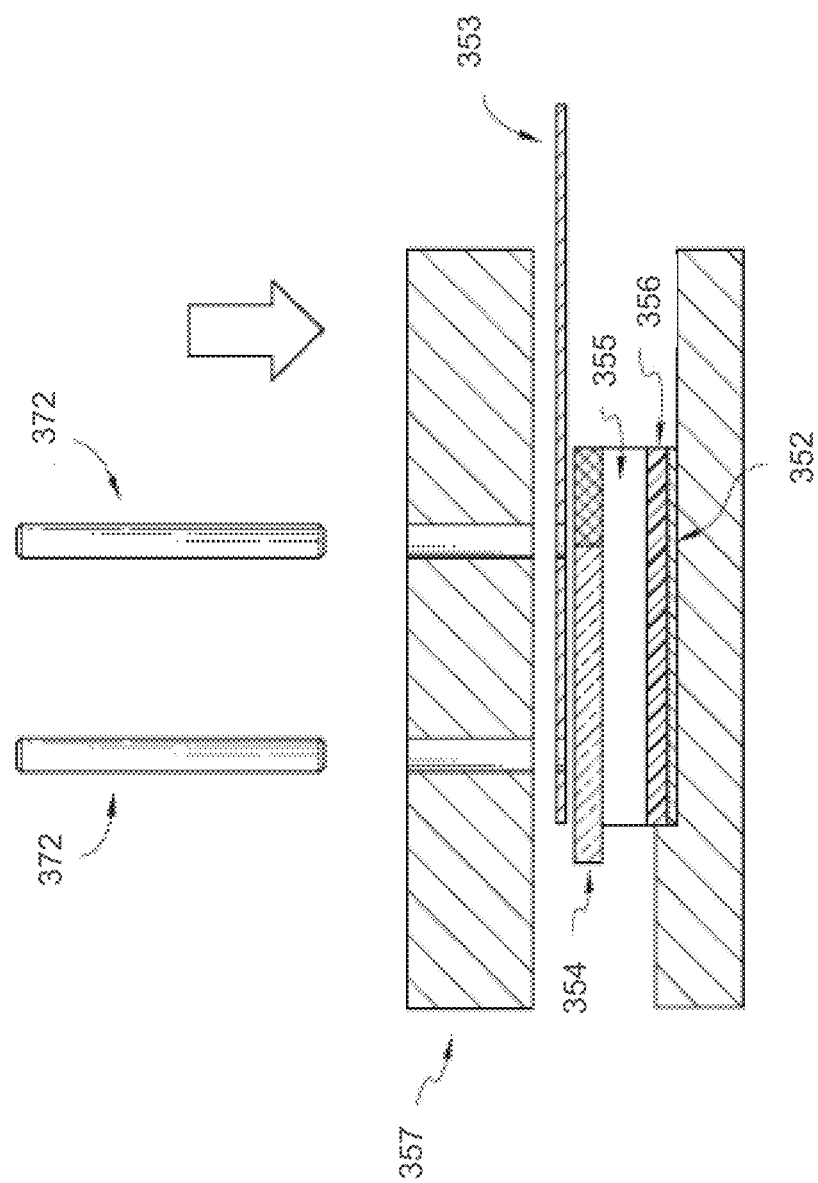

FIGS. 3C-3D illustrate an embodiment of moving pins used to compress the metering stack and assay stack when the cartridge is inserted into an assay reader. As illustrated in FIGS. 3C-3D, moving pins can be used to compress the metering stack 354 onto the assay stack 356. FIG. 3C illustrates the cartridge with the base 352 and cap 353 within the assay reader 357. Moving pins 372 can be used within the assay reader 357 to compress the metering stack 354 and spacer material 355 so that the metering stack 354 can come into contact with the assay stack 356. The moving pins 357 can move downward in the direction of arrow shown in FIG. 3C to compress the metering stack 354 onto the assay stack 356. In some embodiments, the moving pins can pass through a portion of the cap 353 as shown in FIG. 3D. As illustrated in FIGS. 3C-3D, in some embodiments, the moving pins can move vertically within the assay reader 357.

In some embodiments, the target analyte is blood, and the cartridge can be used to collect a sample of blood from a skin prick and deliver the sample to the assay stack consistently with minimal user intervention. The user, with a regular pricking lancet, can elicit bleeding in a suitable body site such as a fingertip, palm, hand, forearm, belly etc. Once a drop of blood of sufficient volume is on the skin, the user can collect it by touching the tip of the cartridge to the blood drop. Once the metering stack is fully filled with blood, the user can insert the cartridge into the assay reader, which triggers the delivery of the blood sample to the assay stack. In some embodiments, this can be performed by a patient, administrator, or healthcare provider. The blood collection and testing as described herein does not have to be performed by a trained heath care professional.

In addition, the cartridge design can allow for dispensing different pre-defined volumes of blood sample to multiple assay locations, without using any moving parts such as pumps or valves in the cartridge or in the assay reader. This increases the accuracy and flexibility of a multiplexed quantitative POC analysis, while reducing the complexity and cost of the cartridge and the assay reader.

Typically, as illustrated in FIG. 2C, the metering stack 224 comprises a channel 230 to contain the target analyte (e.g., blood sample). In certain embodiments, the channel can hold a volume of target analyte in the range of about 0.5 to about 100 µl, about 5 µl to about 90 µl, about 10 to about 80 µl, about 20 µl to about 60 µl or about 30 µl to about 50 µl. The volume of the target analyte can be controlled by the dimensions of the channel, including the shape, width, length, and depth of the channel, as described herein. In some embodiments, the depth of the channel can be in the range of about 5 µm to about 3 mm, about 10 µm to about 2 mm, or about 250 µm to about 1 mm. In some embodiments, the width of the channel can be in the range of about 100 µm to about 10 mm, about 250 µm to about 5 mm, about 500 µm to about 3 mm, or about 750 µm to about 1 mm. In certain preferred embodiments, the dimensions of the channel are selected such that the target analyte is drawn into the channel by capillary action.

Figure 4B:
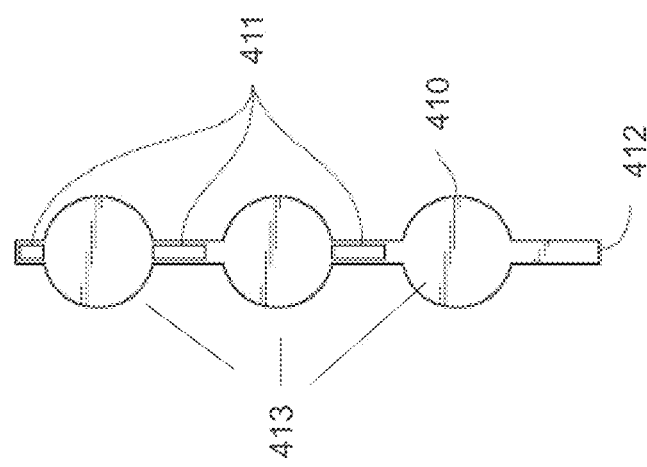
FIG. 4A-5B illustrate embodiments of channels within a metering stack.
Figure 4A:
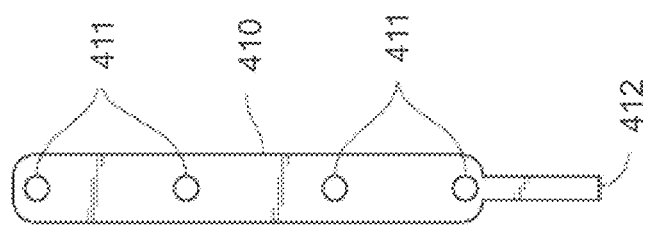

The material of the metering stack 224 can, in some embodiments, form one or more fluid collecting chambers, or receiving chambers, along the length of the channel. FIGS. 4A-5B illustrate embodiments of the channel(s) 410 within the metering stack. As shown in FIGS. 4A-5B, the shape of the channel is not particularly limited and will vary based on the requirements of the assay components in the corresponding assay stack. In some embodiments, the longitudinal cross section of the channel, in a plane parallel to the layered components of the cartridge, can be a rectangle with a constant width or a combination of different rectangular, circular, oval, and/or other shapes. FIG. 4A illustrates one embodiment in which the channel 410 has a rounded rectangular longitudinal cross section. FIG. 4B illustrates a channel 410 with a combination of rectangular portions and circular portions, the latter of which corresponds to receiving chambers located along the length of the channel. The channel 410 can have an inlet 412 where the target analyte sample can be inserted or drawn in (e.g., by capillary action) to fill the channel 410.

The channel may also comprise one or more venting holes 411 that connect the channel to the atmosphere. An example of such a configuration is illustrated in FIG. 4A, which shows channel 410 with a plurality of venting holes 411 arranged along the length of channel 410 and a channel inlet 412. In addition, as indicated in FIG. 4B, channel 410 may comprise one or more receiving chambers 413 for collecting and temporarily storing one or more predetermined volumes of the target analyte prior to introducing the target analyte to the assay components in the assay stack. In certain embodiments, the predetermined volumes of the receiving chambers are such that they permit temporary storage and subsequent delivery of a greater volume of the target analyte than a channel without such receiving chambers (cf. FIGS. 4A and 4B). When channel 410 comprises one or more receiving chambers 413, such venting holes 411 may be disposed along the portions of the channel 410 between the receiving chambers 413, as illustrated in FIG. 4B. However, in other embodiments, the venting holes may be coincident with the receiving chambers. In general, the venting holes release air bubbles that may be trapped in the channel during collection of the target analyte (e.g., blood) thereby helping to distribute the target analyte sample in the channel and facilitating subsequent distribution of the target analyte (or a portion thereof) to the assay components in the assay stack. If desired, the metering stack can include one channel or multiple channels sharing a same channel inlet 412. FIG. 4C illustrates an embodiment with multiple channels 410 in a metering stack, each equipped with venting holes 411. The multiple channels 410 are fluidly connected and can be filled with the target analyte via common channel inlet 412.

Figure 5B:
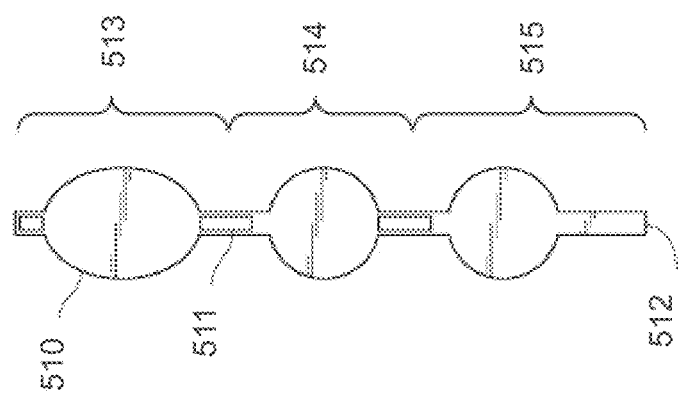
Figure 5A:
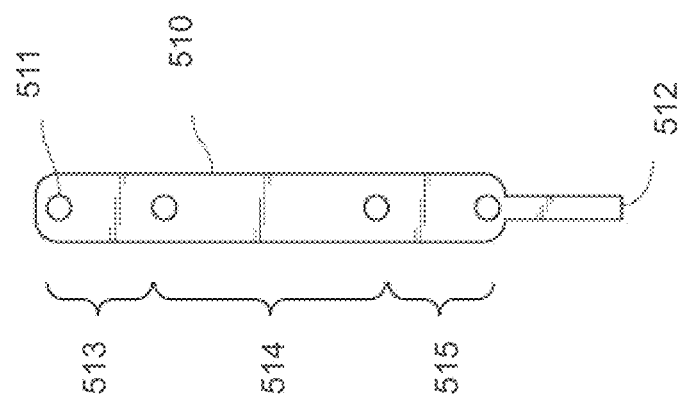

FIGS. 5A-B illustrate two exemplary embodiments of channels according to the invention. In FIG. 5A, channel 510 has venting holes 511 which are arranged along the length of channel 510 at uneven intervals 513, 514, and 515. When the target analyte is admitted into channel 510 via channel inlet 512, this configuration permits different volumes of the target analyte to be delivered to the respective assay components. If desired, the segment between venting holes 511 can hold a volume of target analyte in the range of 0.5-25 µl for each assay. Alternatively, as shown in FIG. 5B, channel 510 may be equipped with a plurality of receiving chambers 513, 514, and 515 which have different predetermined volumes to permit delivery of different volumes of the target analyte to the respective assay components.

Figure 6:
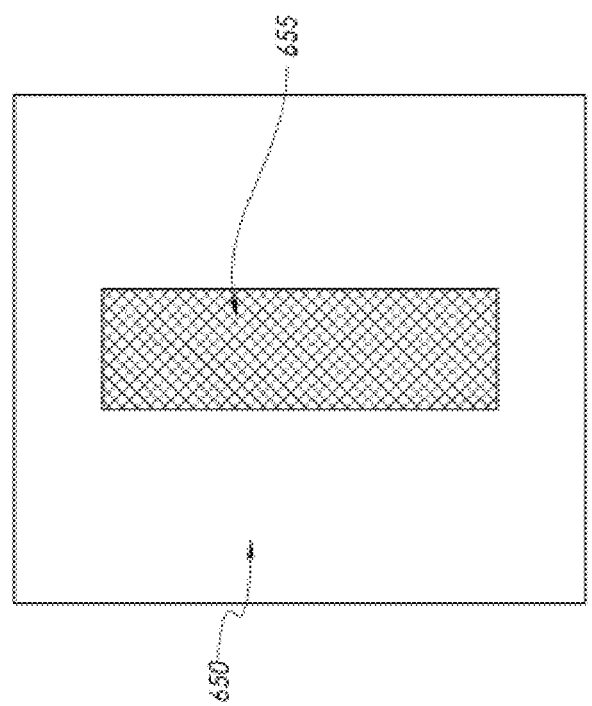
FIG. 6 illustrates an embodiment of a layer of the metering stack that includes a mesh or porous material within a portion of the layer.

Preferably, the metering stack is designed to direct the target analyte fluid to flow into the channel and into any receiving chamber(s) that may be present. In some embodiments, the channel can be formed of or coated with a hydrophilic material, non-limiting examples of which include 93210 hydrophilic PET (Adhesives Research, Glen Rock Pa.) or 9984 Diagnostic Microfluidic Surfactant Free Fluid Transport Film, 9960 Diagnostic Microfluidic Hydrophilic Film, or 9962 Diagnostic Microfluidic Hydrophilic Film (3M Oakdale, Minn.). The channel can also have one or more porous or mesh material along at least some portions of the channel that allows at least a portion of the target analyte to be dispensed from the channel of the metering stack to contact assay components in the assay stack. One non-limiting embodiment is shown in FIG. 6. FIG. 6 shows a plan view of metering stack layer 650 that comprises porous or mesh material 655 which is positioned such that it is aligned with the channel portion on its top surface and the assay distribution ports and assay components on its bottom surface. In some embodiments, the porous or mesh material is selected such that the pores in such material separate the target analyte into a portion that is to be delivered to the assay components and a portion that is not delivered to the assay components. For example, when the target analyte is blood, the pores of the porous or mesh material may be of a size that is suitable for separating erythrocytes from other blood components, such as plasma. In this way, when the cartridge is inserted into the assay reader to perform the assays, only plasma is delivered to the assay components for analysis. Of course, combinations of porous or mesh materials may be used such that the entire target analyte is delivered to some of the assay components, while only portions of the target analyte may be delivered to other assay components. For example, the combination of porous or mesh materials may allow only plasma to reach some assay components, but allow for the delivery of all blood components to other assay components. In certain embodiments, the channel can include a porous or mesh material at the bottom of the channel. The porous or mesh material at the bottom of the channel can be a hydrophilic material or a material coated with a hydrophilic coating. In some embodiments, the porous or mesh material can have a pore size between about 1 µm to about 500 µm. Advantageously, when the target analyte is blood, the pores of the porous or mesh material can be sized to allow the porous or mesh material to hold the blood sample in the channel without dripping during blood collection and to be absorbed by the assay stack during the blood dispensing step which occurs upon insertion of the cartridge into the assay reader.

In some embodiments, the porous or mesh material can also be used to release air and prevent bubble formation during the time that channel is filled with the target analyte. In some embodiments, the channel has a round or octagonal transverse cross-section, as illustrated in FIG. 7A, and in such embodiments, the upper-most layer may have venting holes that are off-set to the side. In FIG. 7A, the venting hole 711 can be disposed at a 45-degree angle relative to the top surface of the cartridge and the mesh or porous material 703 can be positioned on the bottom of the channel. In such a configuration, air may escape from venting hole 711 or through porous mesh 703 as the channel becomes filled with the target analyte. In some embodiments, as illustrated in FIG. 7B, the venting holes 711 can be positioned on the bottom of the metering stack 704 within or near a mesh or porous material 703. As illustrated in FIG. 7B, the channel of the metering stack may have one side open to receive the target analyte. In some embodiments, the channel inlet itself can be one of the venting holes of the channel and, optionally, the end of the channel opposite the channel inlet can be open to the environment and serve as a venting hole for additional air to escape. In some embodiments, as illustrated in FIG. 7C, the venting holes 711 can be positioned on the top the channel 710 and the mesh or porous material 703 can be positioned on the bottom of the channel 710.

Figure 8:
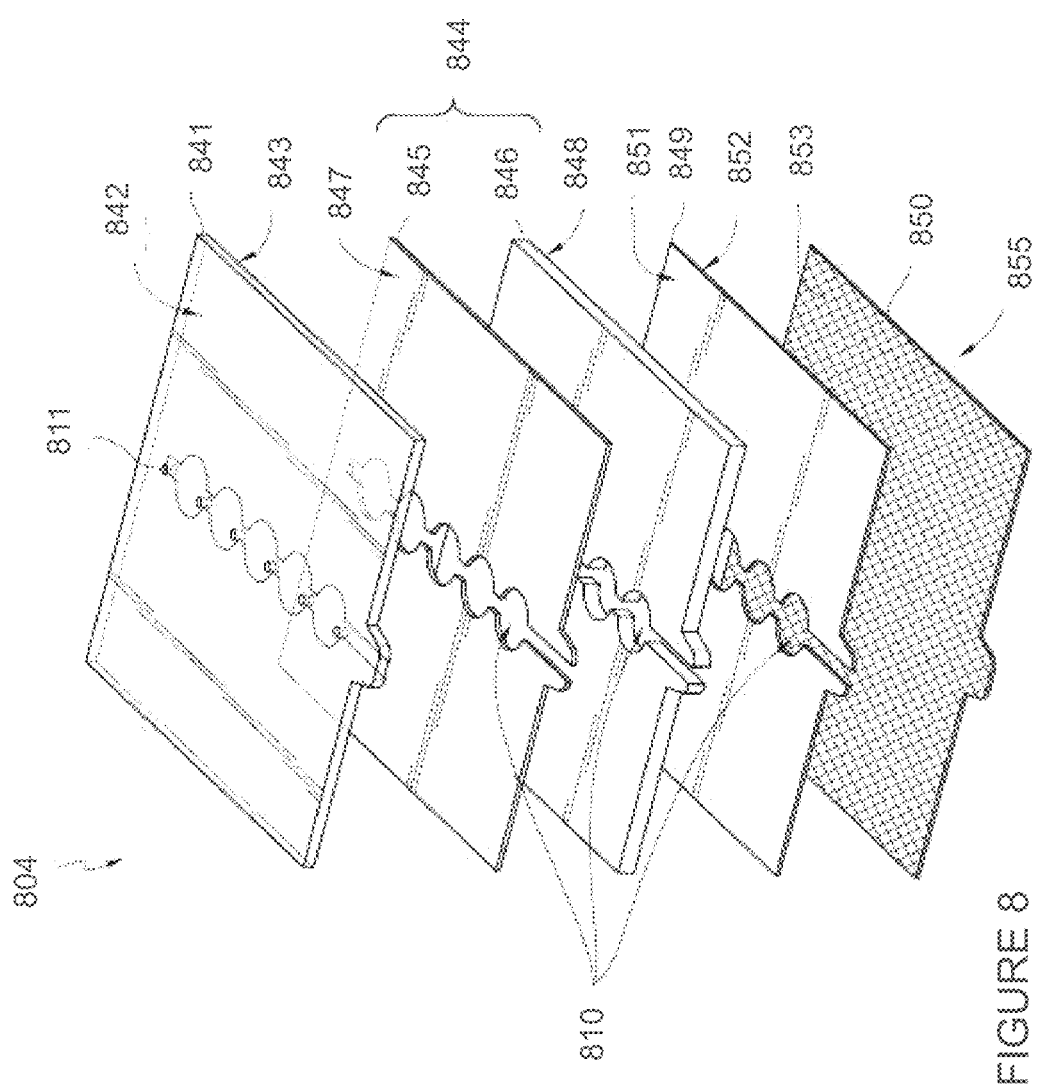
FIG. 8 illustrates various layers of a metering stack, according to some embodiments.

FIG. 8 illustrates an exploded view of a metering stack according to one exemplary embodiment of the invention. In FIG. 8, the metering stack 804 is formed by assembling multiple layers. The first layer 841 can be a plastic sheet with a first side 842 in communication with the surrounding environment when the cartridge is located outside the assay reader and a second side 843 that faces the assay stack. In some embodiments, the first layer 841 may be a cover layer or top layer of the metering stack. In preferred embodiments, first layer 841 may have a hydrophilic surface or coating on second side 843. Non-limiting examples of suitable hydrophilic surfaces coatings include polyvinylpyrrolidone-polyurethane interpolymer, poly(meth)acrylamide, maleic anhydride polymers, cellulosic polymers, polyethylene oxide polymers, and water-soluble nylons or derivatives thereof, to name just a few. The presence of the hydrophilic surface or coating on second side 843 helps to draw the target analyte into the channel, since most, if not all, of the target analytes are aqueous mixtures, such as blood. The first layer 841 may include vent holes 811 positioned to align with the channel 810 defined by the layers below. In FIG. 8A, for example, the vent holes 811 are aligned with the receiving chambers of channel 810 to allow air that otherwise would be trapped as an air bubble in the receiving chamber during channel filling to escape efficiently into the surrounding environment. It should be noted that the channel opening can also serve as a vent hole, if desired. In certain preferred embodiments, the first layer 841 comprises polyethylene terephthalate (PET) with a hydrophilic coating on the second side 843 and with venting holes 811.

The second layer 844 is positioned below the first layer 841 on the second side or assay facing side of the first layer 841. The second layer 844 itself can be a combination of one or more layers as illustrated in FIG. 8. Regardless of whether second layer is comprised of one layer or more than one layer, the second layer essentially defines the shape and size of channel in the metering stack, including any receiving chambers that may be part of the channel. For example, the second layer 844 can be formed from one or more layers of polymeric material cut to define the volume and shape of the channel 810 that can contain the target analyte. Other non-limiting methods of forming the channel 810 include injection-molding, stamping, machining, casting, laminating, and 3-D printing. Combinations of such fabrication techniques are also expressly contemplated by the invention. In the embodiment shown in FIG. 8, second layer 844 has a first side 847 facing the first layer 841 and an opposite second side 848 that faces the assay stack. Furthermore, second layer 844 comprises adhesive layer 845 and plastic layer 846. Adhesive layer 845 fastens first layer 841 to plastic layer 846. In some embodiments, the second layer 844 can be a combination of one or more layers of plastic sheet(s) 846 and adhesive layers 845. Preferably, adhesive layer 845 or plastic layer 846 or both are fabricated from materials which present a hydrophilic surface to the interior surfaces of the channel 810 in order to facilitate the distribution of the target analyte within channel 810. In some embodiments, the hydrophilic plastic sheet(s) can include a PET material with a channel 810 cut into it. If desired, channel 810 may include one or more receiving chambers as shown in FIG. 8. Thus, the thickness and geometry of channel 810 can control the volume of sample to be collected. The hydrophilic interior surfaces of the channel 810 allow the metering stack to collect blood sample by capillary force. In some embodiments, the first layer 841 and the second layer 844 can be one integrated layer used in the metering stack.

In FIG. 8, third layer 849 can be formed from a hydrophobic adhesive layer. Non-limiting examples of suitable materials for fabricating third layer 849 include 3M 200MP adhesive or 3M 300MP adhesive (3M, Oakdale, Minn.). In preferred embodiments, the same channel geometry as channel 810 is cut into the third layer to match channel 810 cut in the second layer. In some embodiments, the third layer 849 can have a first side 851 facing the second layer 844 and an opposite side 852. In some embodiments, the third layer 849 can define the hydrophilic region in a fourth layer 850 positioned below or on the second side 852 of the third layer.

In some embodiments, the fourth layer 850 can be a hydrophilic mesh or porous material. In some embodiments, substantially all of the fourth layer 850 can include the mesh or porous material as shown in FIG. 8. In other embodiments, the hydrophilic mesh or porous material can be a portion of the fourth layer 850 as shown in FIG. 6. More specifically, FIG. 6 illustrates an embodiment of a fourth layer of the metering stack that includes a mesh or porous material within the portion of the fourth layer that aligns with the channel formed from the second and third layers. In some embodiments, such as the example shown in FIG. 8, the fourth layer 850 can have a first side 853 facing the third layer 849 and an opposite assay stack facing second side 854. The hydrophobic third layer 849 can be positioned above the fourth layer 850. The hydrophobic third layer 849 can be a hydrophobic adhesive layer to define a wettable region of the mesh or porous material of the fourth layer 850.

The method used to fabricate the metering stack is not particularly limited, so long as it is compatible with the general manufacturing requirements for medical devices. In certain embodiments, the layers that constitute the metering stack are first fastened together as large multilayer sheet or strip which is then subjected to stamping or cutting processes to form the metering stack, including the channel and any receiving chambers that may be present. In some embodiments, the first layer 841 and second layer 844 can be combined in one piece of plastic material with a hydrophilic surface forming the channel. In some embodiments, the third layer 849 and fourth layer 850 can be combined in one piece of patterned mesh made by printing or other method to define the hydrophilic porous area. In some embodiments, the third layer is not used in the metering stack. Various other combinations of two or more layers, as well as additional layers, are contemplated by various embodiments.

In the assay systems of the invention, the assay reactions occur in the assay stack. In general, an assay stack comprises one or more "assay components." As used herein, the term "assay component" refers to one or more of the active component and a passive supporting element or mask, including but not limited to the multiplexed assay pads. The number assay pads in a particular assay component is not particularly limited and is scalable to meet the assay requirements needed to diagnose the condition of the patients for whom the assay stack is designed. In preferred embodiments, the top layers of the assay pads of a given assay component align vertically with the appropriate regions of the channel in the metering stack above to ensure that a predetermined volume of target analyte, sufficient to perform the assay associated the particular assay, is delivered to the assay pad. The assay pad can act as a sponge that draws the sample through the mesh of the metering stack into the assay stack, for example through capillary action, gravity, etc. Therefore, once the metering stack and the assay stack are in contact with or within close proximity to each other, the fluid from the target analyte sample to be analyzed is directed to move into the assay pad, where it may encounter one or more chemical reagents required to perform the assay associated with the particular assay component. If desired, the assay stack may comprise additional layers that contain the chemicals required for the completion of the assay. The number of layers required can depend on the number of chemical reactions that need to take place to complete the assay. For instance, some assays require a single layer while others may require multiple layers. In various embodiments, layers of the assay stack can be made of variously-shaped and variously-sized pads of different porous membrane materials, non-limiting examples of which include nylon, polyethersulphone (PES), nitrocellulose, cellulose filter paper, and glass fiber.

The type of assays that may be formed using the assay systems of the invention are not particularly limited and can be any assay for which the required reagents can be stably incorporated into one or more assay pads and which can cause a change that can be detected by the assay reader. In preferred embodiments, the assay reactions cause a color change, which may be detected using the colorimetric detection methods as described herein. In certain embodiments, the assays may be porous material-based lateral flow assays, vertical flow assays, and/or a combination of lateral and vertical flow assays. In general, the target analyte is a biological fluid, non-limiting examples of which include blood, saliva, sweat, urine, lymph, tears, synovial fluid, breast milk, and bile, or a component thereof, to name just a few. In certain preferred embodiments, the target analyte is blood or a component thereof (e.g., blood plasma). For example, in one embodiment, the assay systems of the invention are useful for providing diabetic patients with point-of-care information regarding their blood composition, including glucose level, hemoglobin A1C with eAG, C-peptide levels, creatinine levels, and the like. By way of example, glucose levels may be measured by reaction with dinitrosalicylic acid, which results in a color change that is proportional to the amount of glucose present. Alternatively, glucose levels in a target analyte may be analyzed by monitoring the degree of change in yellow color characteristic of ferricyanide. As another example, the presence of creatinine can be detected by reacting creatinine with a picrate, which results in a colored complex. In yet another example, the assay systems may be used to evaluate the immune reactivity of blood platelets using a colorimetric assay chemistry based on the reduction of tetrazolium salts. See, e.g., Vanhée D., et al, "A colorimetric assay to evaluate the immune reactivity of blood platelets based on the reduction of a tetrazolium salt," J. Immunological Methods, Vol. 159, Issues 1-2, Feb. 1993 pp. 253-259. In other embodiments, when the target analyte is urine, the assay stack may comprise assay components for measuring glucose, detecting uric acid, detecting hematuria, or detecting metabolites of illicit drugs, using assay chemistries as known in the art. For instance, when the target analyte is uric acid, an assay monitoring the reduction of cupric copper to cuprous copper, which may in turn complex with the neocuproine to form a colored material that is proportional in density to the concentration of uric acid in the analyzed liquid. See, e.g., U.S. Pat. No. 3,992,158, which is incorporated by reference in its entirety.

In certain embodiments, one or more assay pads in an assay component do not contain any reagents for performing assays on the target analyte, but instead simply absorbs or adsorbs the target analyte to present it for direct analysis using the assay reader of the invention. For example, in certain embodiments, the assay pad absorbs blood plasma that has been separated from the red blood cells of the original blood sample, using the methods described herein, and presents the blood plasma for optical analysis by the assay reader to determine the extent to which hemolysis has occurred.

Figure 9:
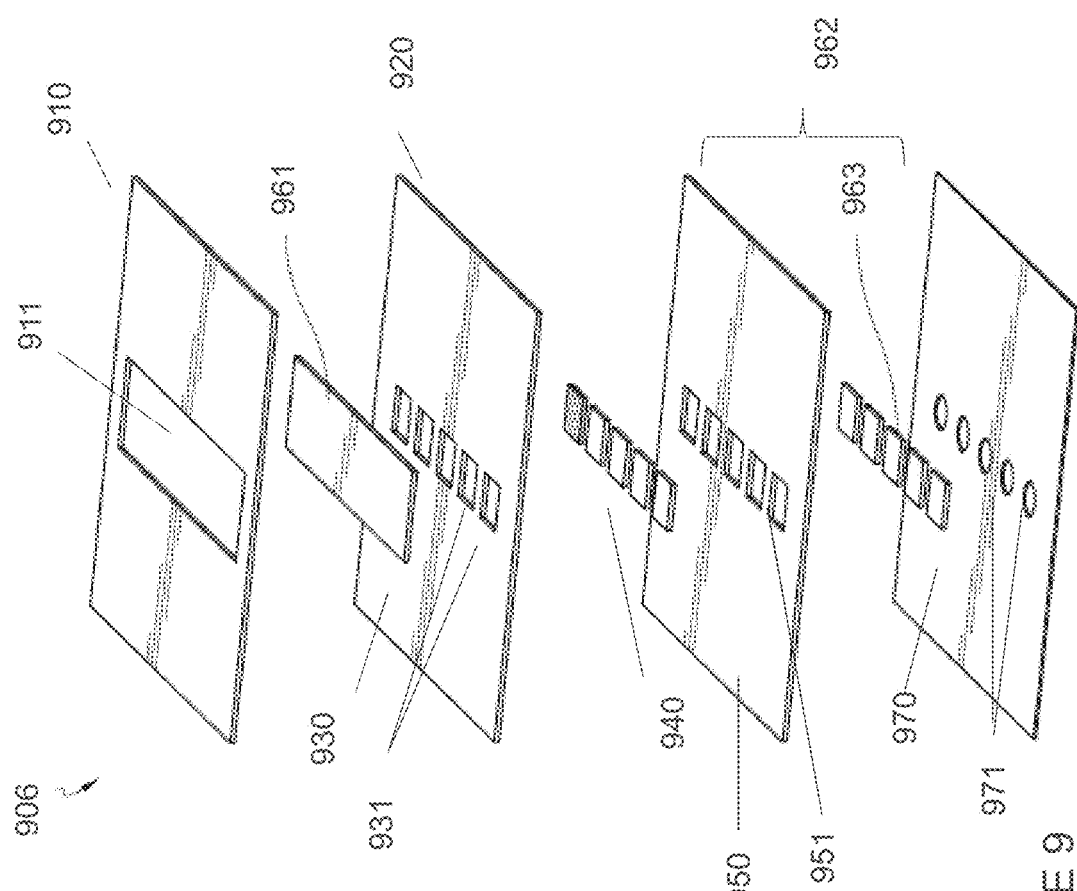
FIG. 9 illustrates various layers of an assay stack, according to some embodiments.

FIG. 9 illustrates an exemplary assay stack 906 according to one embodiment of the invention. In FIG. 9, the assay stack 906 is formed of multiple layers, including one or more of the layers with active components and a passive supporting element or mask. More specifically, in FIG. 9, assay stack 906 comprises assay stack cover layer 910 that features cut-out portion 911 that is aligned with the channel in the overlying assay stack. Generally, assay stack cover layer 910 is fabricated from a polymeric material that provides rigidity to the assay stack and provides ease of handling during manufacturing of the cartridge. Furthermore, cut-out portion 911 allows the target analyte to flow past assay cover layer 910 towards the under assay components when the cartridge is inserted into the assay reader, as described herein. In some embodiments, the assay stack 906 comprises a separation layer 961 in the top most layer facing the metering stack, although this invention also expressly contemplates embodiments in which an assay stack comprises a plasma separation layer which is not in the top most layer of the assay stack. It should be noted that the separation layer is optional, and that in certain embodiments, the assay stack does not comprise any separation layer. When present, separation layer 961 may be used to separate components of the target analyte to prevent undesirable components of the target analyte from reaching the underlying assay components. For example, when the target analyte is blood, the separation layer 961 may be a plasma separation membrane that prevents erythrocytes from reaching the assay components after the cartridge has been inserted into the assay reader. This is advantageous because the strong spectral absorption by the hemoglobin present in erythrocytes may overwhelm the color changes that occur at the assay pad after the assay is performed. Such a plasma separation membrane can be made of a variety of materials, non-limiting examples of which include an asymmetric polysulphone membrane, glass fiber, or cellulose. In some embodiments, the fabrication of the plasma separation membrane can include surface treatments for improved wettability and/or other properties. The plasma separation layer can be one continuous piece of membrane for all of the assay components, or multiple pieces of membrane material that may be same or different (or some combination thereof) for each of the assay pads in the assay component in the assay stack FIG. 9. In some embodiments, some of the assay pads of an assay component have a corresponding plasma separation layer, while other assay pads do not have such a layer.

In FIG. 9, assay stack 906 includes assay component 920, which features mask support layer 930 with a plurality of cut-outs 931 that are configured to receive and immobilize assay pads 940 when the assay stack 906 is assembled. Preferably, cut-outs 931 are positioned laterally in mask support layer 930 such that each of the assay pads 940 are aligned with both the channel and the porous or mesh material of the metering stack above in order to receive predetermined volumes of target analyte sufficient to perform the assay reaction associated with the given assay pad. As shown in FIG. 9, in some embodiments, the assay stack 906 can include a second assay component 962 positioned below the plasma separation layer 961 and first assay component 920. The second assay component 962 comprises a mask support layer 950 with a plurality of cut-outs 951 that are configured to receive and immobilize assay pads 963 when the assay stack 906 is assembled. Preferably, cut-outs 951 are positioned to align assay pads 963 with assay pads 940, such that the target analyte will flow from assay pads 940 into assay pads 963. Assay pads 963 may comprise chemical reagents that are necessary to complete the assay reactions that are initiated when the target analyte flows through the assay pads 940 of assay component 920. In other embodiments, one or more of assay pads 963 are non-functional pads that do not cause any further chemical reactions with the target analyte and merely transmit the completed assay products to the bottom of the assay stack for analysis by the assay reader. In some embodiments, assay pads 963 serve as a detection indicator layer that provides information corresponding to the results of the assay performed. For example, assay pads 963 can include a visual indicator, such as a color change, to indicate the results of the assays. Furthermore, while assay stack 906 in FIG. 9 contains only two assay components 920 and 962, it should be understood that the assay stack 906 may contain additional assay components with assay pads that are impregnated with chemical reagents that are required to complete and/or report the results of a particular assay. For instance, the assay stack 906 can include any number of assay components necessary to perform the analysis of the blood sample. Because some assays require more chemical steps than others, assay components near the bottom of the assay stack may comprise more non-functional assay pads which only serve to draw the completed assay products to the bottom of the assay stack, where the results may be detected by the assay reader, as described herein.

Assay stack 906 in FIG. 9 also includes an assay bottom layer 970, which is typically fabricated from a polymeric material to provide mechanical strength and ease of handling of assay stack 906 during the manufacturing process. In addition, assay bottom layer 970 typically comprises a plurality of detection ports 971 which are aligned with the assay pads of the assay stack and sized to permit interrogation of the assay results by the assay reader. For example, as described herein, the assay reader may probe the assay results by shining light of a particular wavelength onto the assay pads of the bottommost assay component in the assay and detecting the intensity or wavelength of the light that is scattered from the assay pads.

Figure 10:
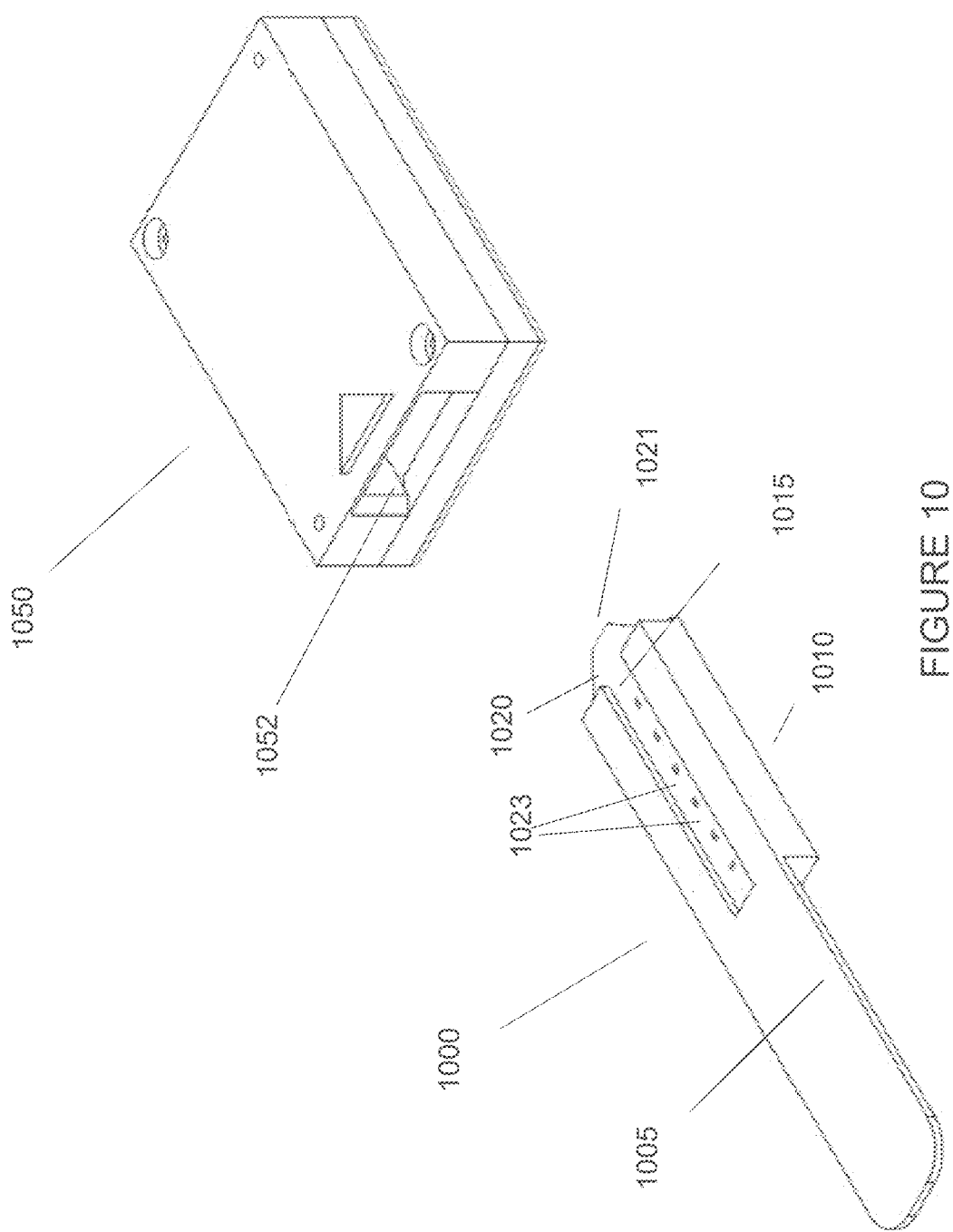
FIG. 10 illustrates a cartridge and an assay reader, according to some embodiments of the invention.

FIG. 10 comprises a cartridge 1000 and an assay reader 1050 according to another embodiment of the invention. Cartridge 1000 features a unitary outer shell that includes handle portion 1005 and housing portion 1010. In this embodiment, handle portion 1005 is a long, thin tab that permits easy handling of the cartridge 1000 by user, even when the user is using only one hand. As shown in FIG. 10, cartridge 1000 further comprises metering stack 1020 which is partially exposed when it is inserted into housing portion 1010. In particular, channel inlet 1021 protrudes slightly from the housing portion 1010, such that the mouth of the channel 1021 may be dipped into the target analyte, causing the target analyte to be drawn into the channel of metering stack 1020. A plurality of venting holes 1023 are visible on the top layer of metering stack 1020 and are aligned with the underlying channel of the metering stack 1020. The venting holes 1023 prevent the formation of undesirable air bubbles in the channel while the channel is being filled with the target analyte. Not shown is a corresponding assay stack, which is positioned underneath metering stack 1020.

Figure 11:
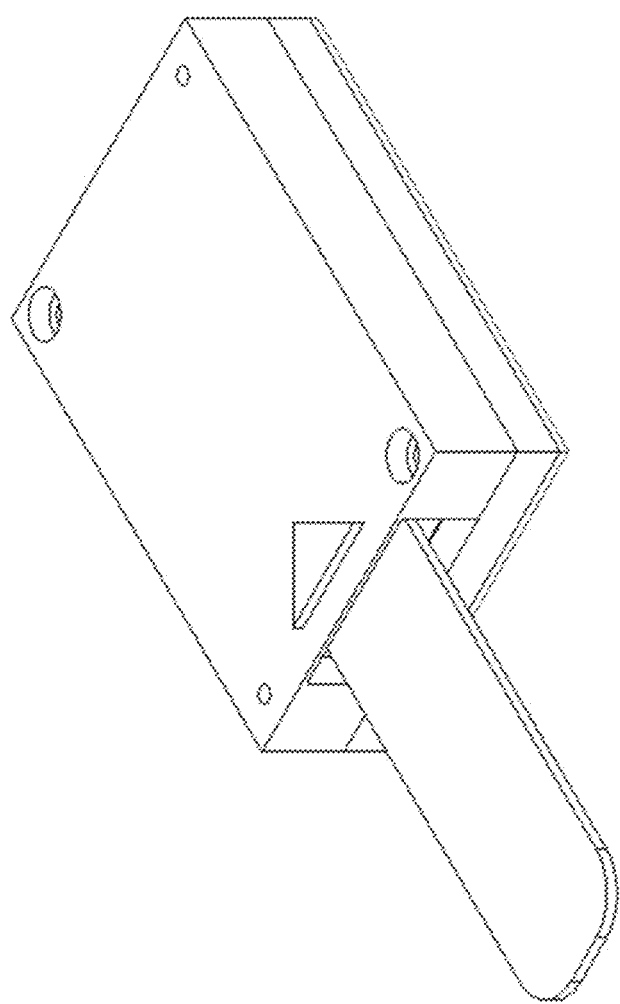
FIG. 11 illustrates a cartridge inserted into an assay reader according to an embodiment of the invention.

After the channel of metering stack 1020 is filled with the target analyte, cartridge 1000 is inserted into assay reader 1050 (FIG. 11). As shown in FIG. 10, cartridge 1000 features a slot 1015, which is configured to receive an internal tab that extends along the longitudinal direction of assay reader 1050. The internal tab protrudes downward into the receiving chamber 1052 assay reader 1050, creating a rudimentary "lock and key" mechanism that makes it impossible for the user to inadvertently insert cartridge 1000 upside down into assay reader 1050. In addition, when the cartridge 1000 is inserted into assay reader 1050 after the target analyte has been collected, the internal tab provides a compressive force that compresses together the metering stack 1020 and the underlying assay stack, thereby initiating the assay reactions, as described herein.

Figure 12:
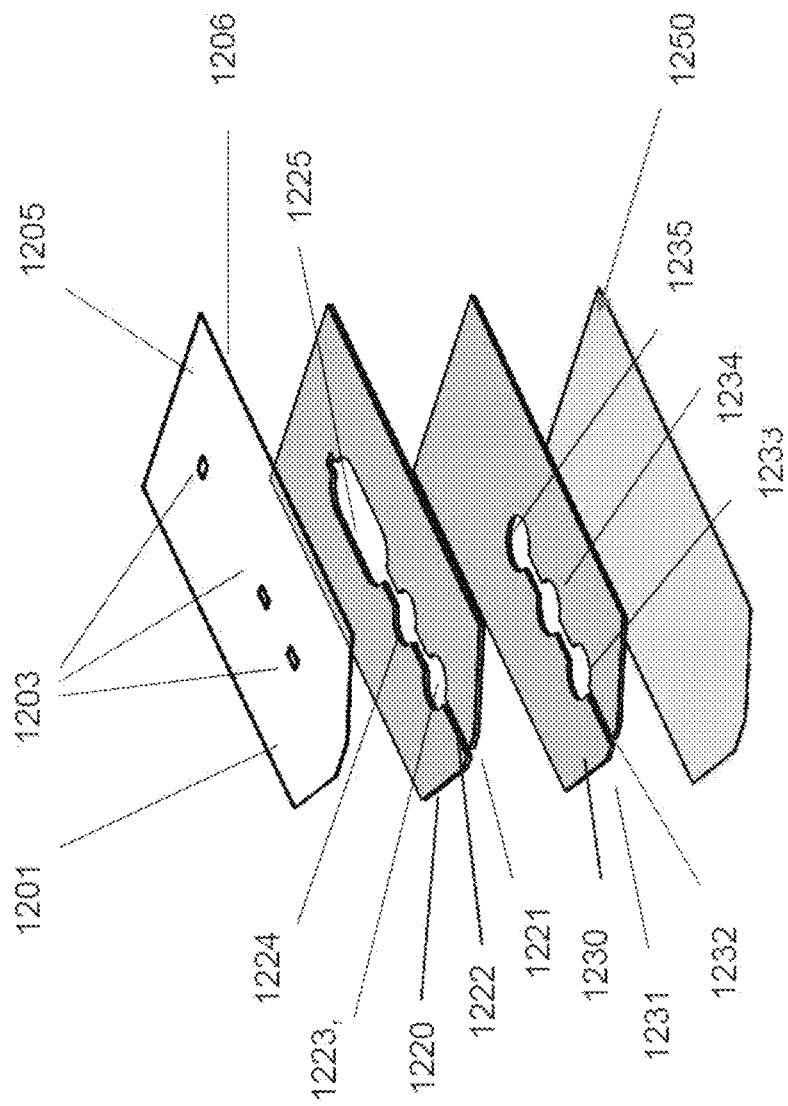
FIG. 12 illustrates a metering stack of a cartridge according to one embodiment of the invention.

FIG. 12 shows an exploded view of metering stack 1020 corresponding to the embodiment of the cartridge shown in FIG. 10. Top layer 1201 comprises a polymeric sheet with venting holes 1203 that are aligned with the underlying channel in the metering stack. In certain preferred embodiments, the surfaces of top layer 1201 may be subjected to chemical treatments that facilitate the collection of the target analyte. For instance, when the target analyte is blood, it is advantageous to apply a hydrophobic coating 1205 to the top surface of top layer 1201 and a hydrophilic coating 1206 to the bottom surface of top layer 1201. In this way, during blood collection, the hydrophobic top coating 1205 on top layer 1201 prevents the blood from sticking to the exposed top surface of the metering stack in the cartridge. On the other hand, the hydrophilic bottom coating 1206 of the top surface 1201 helps to draw the blood into the metering stack when channel inlets 1221 and 1231 are brought into contact with the blood, because the hydrophilic coating allows the blood to wet the bottom surface of top layer 1201 as the channel fills. The metering stack in FIG. 12 further includes an upper channel layer 1220 and a lower channel layer 1230. Upper channel layer 1220 includes channel 1222 which has channel inlet 1221 and three receiving chambers 1223, 1224, and 1225. As shown in FIG. 12, receiving chamber 1225 is larger than receiving chambers 1223 and 1224 and therefore capable of holding a larger volume of the target analyte when the chamber is filled. Lower channel layer 1230 comprises channel 1232 with channel inlet 1231 and three receiving chambers 1233, 1234, and 1235. In certain preferred embodiments, the top surface of lower channel layer 1230 is coated with a hydrophilic coating, which helps to draw the target analyte (e.g., blood) into channels 1222 and 1232 by permitting the target analyte to wet the top surface of lower channel layer 1230. In certain preferred embodiments, the bottom (assay stack facing) surface of lower channel layer 1230 is coated with a hydrophobic coating, which helps to localize the target analyte in receiving chambers 1233, 1234, and 1235 both during collection and when the metering stack is compressed by the assay reader to drive the target analyte into the underlying assay stack for analysis. At the bottom of the metering stack shown in FIG. 12 is porous hydrophilic layer 1250, which prevents the target analyte from contacting the underlying assay stack until the metering stack and assay stack are compressed together as a result of insertion into the assay reader.

Figure 13B:
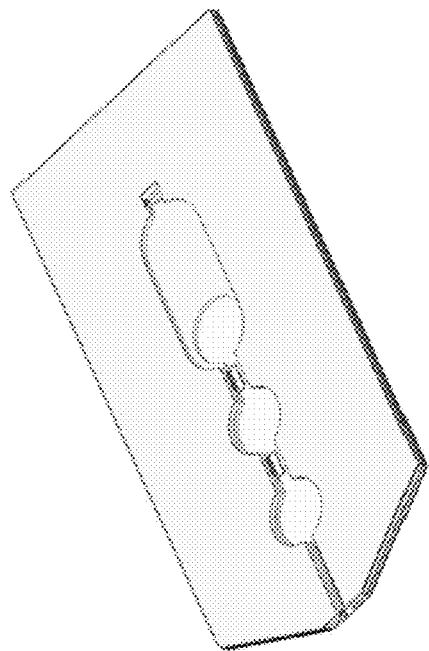
FIGS. 13A-B illustrates an assembled metering stack according to one embodiment of the invention.
Figure 13A:
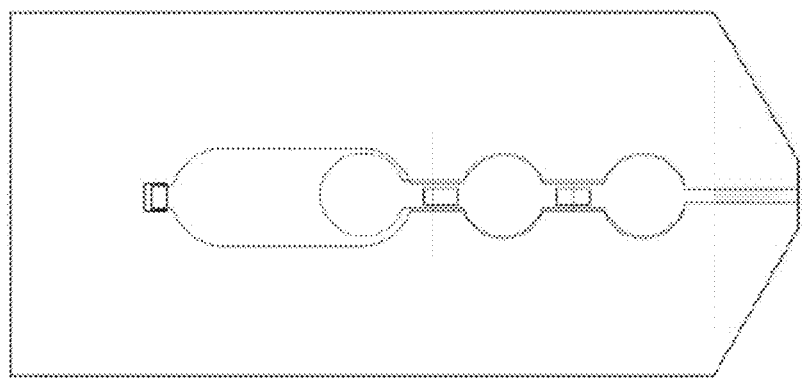

In the "dual channel" configuration shown in FIG. 12, upper channel layer 1220 and lower channel layer 1230 are aligned such that they are in fluid communication when the metering stack is assembled. Preferably, the receiving chambers of upper channel layer 1220 and lower channel layer 1230 coincide, as shown in the FIG. 13A (top view) and FIG. 13B (perspective view). Thus, the channel and 1222 receiving chambers 1223, 1224, and 1225 in upper channel layer 1220 serve as reservoirs of additional target analyte that can be delivered to corresponding receiving chambers 1233, 1234, and 1235 in lower channel layer 1230. In this way, the additional target analyte in upper channel 1222 and corresponding receiving chambers 1223, 1224, and 1225 ensure that a sufficient amount of the target analyte is delivered to the underlying assay stack when the cartridge is inserted into the assay reader. The size of the receiving chambers 1223, 1224, and 1225 may be varied depending on the sample size requirements of the assay pads in the assay stack as described herein. For example, in the non-limiting embodiment shown in FIG. 12, receiving chamber 1225 in upper channel layer 1220 is larger than corresponding receiving chamber 1235 in lower channel layer 1230. This permits different volumes of the target analyte to be delivered as needed to the assay pads in the assay stack below, thereby providing additional flexibility as to the types of assays that may be incorporated in the cartridges of the invention. In addition, the bottom of lower channel 1230 defines the fluid communication region between the channel and the assay pad. In one embodiment, the fluid communication region is the same or smaller than the top surface area of the assay pad.

Figure 14B:
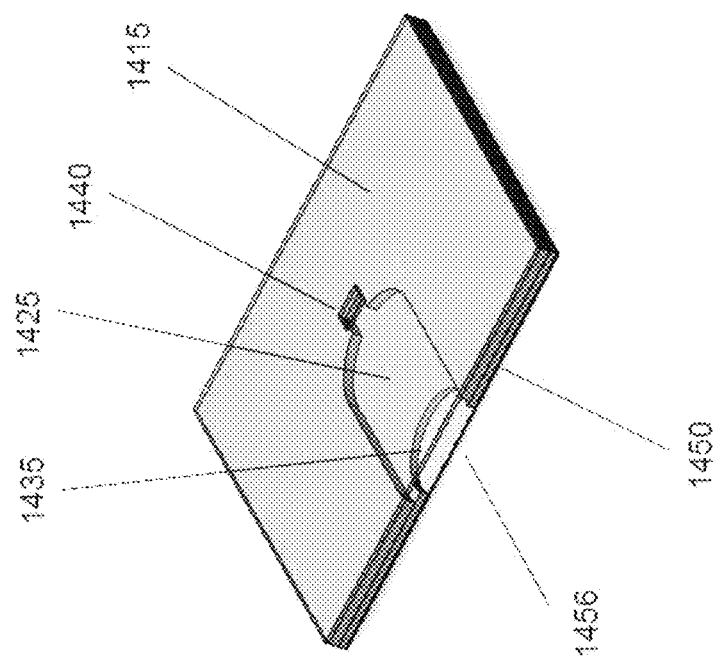
FIG. 14B shows a cross-sectional view of a metering stack and assay stack according to one embodiment of the invention.
Figure 14A:
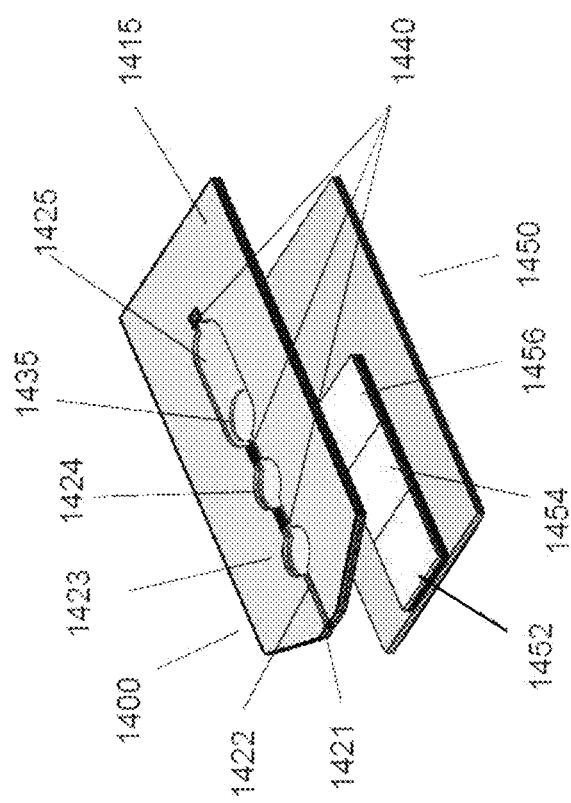
FIG. 14A illustrates a metering stack and an assay stack according to one embodiment of the invention.

FIG. 14A shows metering stack 1400 and corresponding assay stack 1450 before they are assembled together and inserted into the cartridge. In this non-limiting embodiment, metering stack 1400 has a dual-channel construction, with an upper channel layer and lower channel layer as shown in FIG. 12. When metering stack 1400 is assembled, upper channel 1422 with receiving chambers 1423, 1424, and 1425 can be seen through top layer 1415. Venting holes 1440 are aligned with channel 1422 and positioned between receiving chambers 1423 and 1424, between receiving chambers 1424 and 1425, and at the end of channel opposite the channel inlet 1421. Furthermore, receiving chambers 1423, 1424, and 1425 are aligned with the receiving chambers in the lower channel, but only receiving chamber 1435 of the lower channel can be seen readily since receiving chambers 1423 and 1424 are the same size as and coincident with their corresponding receiving chambers in the lower channel. The receiving chambers in the lower channel layer are aligned with corresponding assay pads 1452, 1454, and 1456 in assay stack 1450. This alignment is shown in FIG. 14B, which is a transverse cross-sectional view of metering stack 1400 and assay stack 1450 through upper receiving chamber 1425 and lower receiving chamber 1435 after the metering stack and assay stack have been brought together.

Figure 15C:
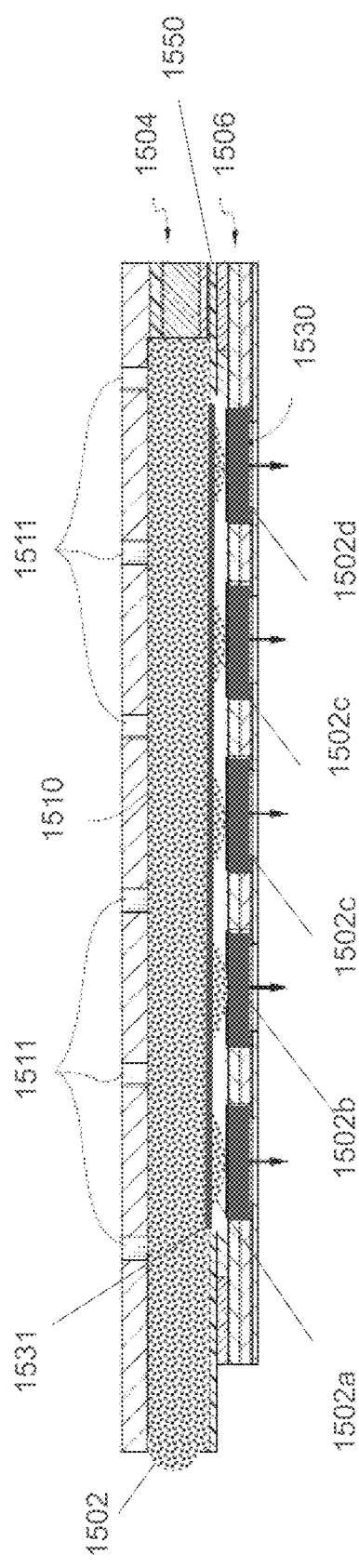

FIGS. 15A-15D illustrate the operation of the cartridge in four steps according to one exemplary implementation of the invention. For clarity, the embodiment shown in FIGS. 15A-15D comprises a metering stack with only a single channel layer. It should be noted, however, that the basic principle of operation is similar for metering stacks with more than one channel, as exemplified in FIGS. 12-14. FIG. 15A illustrates a schematic longitudinal cross sectional view of metering stack 1504 during sample collection. As shown in FIG. 15A, target analyte is distributed on surface 1501, which may be the surface of a patient's skin when the target analyte is blood. During sample collection, the channel 1510 in the metering stack 1504 can be filled with the target analyte (e.g., blood) by exposing channel inlet 1505 to the target analyte 1502. The target analyte 1502 is drawn into channel 1510 by capillary action and/or by gravity, as indicated by arrow 1508. In some embodiments, pointing channel inlet 1505 of the channel 1510 of the metering stack 1504 upwards can help blood flow into the channel 1510. As channel 1510 begins to fill, the air in the channel 1510 is displaced by the target analyte 1502 and driven out of channel 1510 via vent holes 1511, as indicated for one vent hole by the black arrow labeled 1512. In addition, some of the air in channel 1510 may escape via the porous or mesh layer 1550 at the bottom of the metering stack. Furthermore, the presence of the venting holes 1511 and/or porous or mesh layer 1550 also permits any air bubbles introduced into the channel by user error to escape before the sample collection is completed. Such air bubbles may form, for example, if the user accidentally moves channel inlet 1505 outside of the drop of target analyte 1502 on surface 1501 during sample collection. In this way, the venting holes 1511 in metering stack 1504 help to ensure that a predetermined volume of target analyte is reliably delivered to the assay stack below. As shown in FIGS. 15A-D, the metering stack and assay stack can have extra space to allow overdraw of the sample without dispensing the extra sample to the assay pad. In addition, the channel 1510 in the metering stack 1504 may extend beyond the last assay pad to act as a run-off area. If the user keeps filling the channel after the sample reaches the indicator location the excess sample can fill the extra volume in the channel beyond the last pad.

As described herein, the size of the pores or mesh in porous or mesh layer 1550 is selected to ensure that the target analyte does not leak through the porous or mesh layer 1550 during target analyte collection. In some embodiments, channel 1510 comprises a plurality of receiving chambers 1515 located along the length of the channel. Due to the nature of the longitudinal cross section shown in FIG. 15A, the positions of the receiving chambers 1515 are indistinguishable from the rest of channel 1510 and are therefore represented by the dotted lines, which also indicate that receiving chambers 1515 are positioned between vent holes 1511.

In the configuration shown in FIG. 15A, metering stack 1504 is separated from assay stack 1506 by spacing 1525, which may achieved by inserting a compressible spacing material (not shown for clarity) between the metering stack and the assay stack. The compressible spacing material is positioned in spacing 1525 such that it does not interfere with the transfer of the target analyte 1502 from the metering stack to the underlying assay stack 1506. Assay stack 1506 includes a plurality of assay pads 1530 which contain reagents that interact with the target analyte 1502 to provide an assay result when the target analyte is transferred from metering stack 1504 to assay stack 1506. In this exemplary embodiment, assay stack 1506 also features separation layer 1531 which may be used to prevent a portion of the target analyte from reaching the assay pads 1530 (e.g., red blood cells, if the target analyte is blood). Separation layer 1531 may also contain assay reagents that interact with the target analyte 1502. In addition, for each assay pad 1530, separation layer 1531 may be comprised of different materials with different thicknesses and/or reagents contained within, although in this illustrative embodiment, separation layer 1531 is one continuous piece. The assay stack includes one or a plurality of assay pads, which may be used for different functions, non-limiting examples of which include separation of analyte components, assay reactions, or a combination thereof. In some embodiments, the assay stack contains only one or more assay pad with assay reagents, and the assay pads do not function as a separation layer. In certain embodiments, one or more assay pads function as separation layers and do not contain any assay reagents. Of course, the invention also contemplates embodiments where the assay stack contains assay pads that contain reagents and also function as a separation layer. For the purposes of illustration, a gap 1532 is shown between the separation layer 1531 and the assay pads 1530. However, in many (if not most) embodiments, assay pads 1530 will be in direct contact with separation layer 1531, so that the target analyte will be wicked directly into the assay pads when the metering stack and the assay stack are brought together.

The filling of the channel 1510 with target analyte can be judged by indicators on the metering stack 1504. In some embodiments, the indicator can be a visual indicator. For example, the presence of the target analyte (e.g., blood) inside the channel may be visible through a transparent material above or surrounding the channel or at the end of the channel. In other embodiments, the visible indicator can be an indicator initiated when target analyte reaches a particular location in the channel. For example, the visible indicator can be initiated when target analyte reaches the end of the channel. For example, when the target analyte is blood, the top layer of the metering stack 1504 can be designed so that the blood is visible only through a slit at a given location of the channel 1510. Once the blood reaches this location the user can see a "red slit," a "red line," or any other indicator which can be used as a visual cue for a user to know when to stop collecting the sample. In some embodiments, the indicator can be a light emitting diode (LED) that activates when the blood reaches a set point. In some embodiments, the indicator can be activated by electrodes. The electrodes can trigger or activate an alarm, light, or other indictor when the electrodes are in contact with blood in the channel.

FIG. 15B shows metering stack 1504 and assay stack 1506 after the channel 1510 has been filled with target analyte 1502 and inserted into the assay reader, causing the compression of the spacer material between the metering stack 1504 and the assay stack 1506 the removal of gap 1525. In this way, metering stack 1504 and the assay stack 1506 are brought together. At this point, target analyte 1502 is permeating through porous or mesh layer 1550 and separation layer 1531, but has not reached assay pads 1530, as shown by the absence of any target analyte in gap 1532. In certain embodiments, due to the design of metering stack 1504, target analyte 1502 reaches all of the assay pads at essentially the same time. This is illustrated schematically in FIG. 15C, which shows target analyte portions 1502a, 1502b, 1502c, and 1502d permeating porous or mesh layer 1550 and separation layer 1531 and contacting assay pads 1530 in parallel. The synchronization of the assays in the assay stack is advantageous, because many assays require the reagents to react for a certain time before valid assay results can be obtained. By providing a well-defined starting point for the assays, the invention provides a reliable, repeatable system assay system for performing different assays at the same time. It should be noted, however, that the invention also specifically contemplates embodiments where the start of the assays is not synchronized. For example, in certain embodiments, the assay reader comprises sensors which are capable of detecting the actual starting time and ending time by monitoring a signal change as described herein, a non-limiting example of which includes a change in color. When the target analyte 1502 contacts assay pads 1530, the target analyte is drawn or wicked into the assay pads by capillary action and/or gravity, as indicated by the black arrows in FIG. 15C. At this point, vent holes 1511 allow ambient air to enter channel 1510, thereby preventing the formation of a partial vacuum that would otherwise be caused by the absorption of the target analyte 1502 from the channel 1510 into the assay pads 1530 below.

Figure 15D:
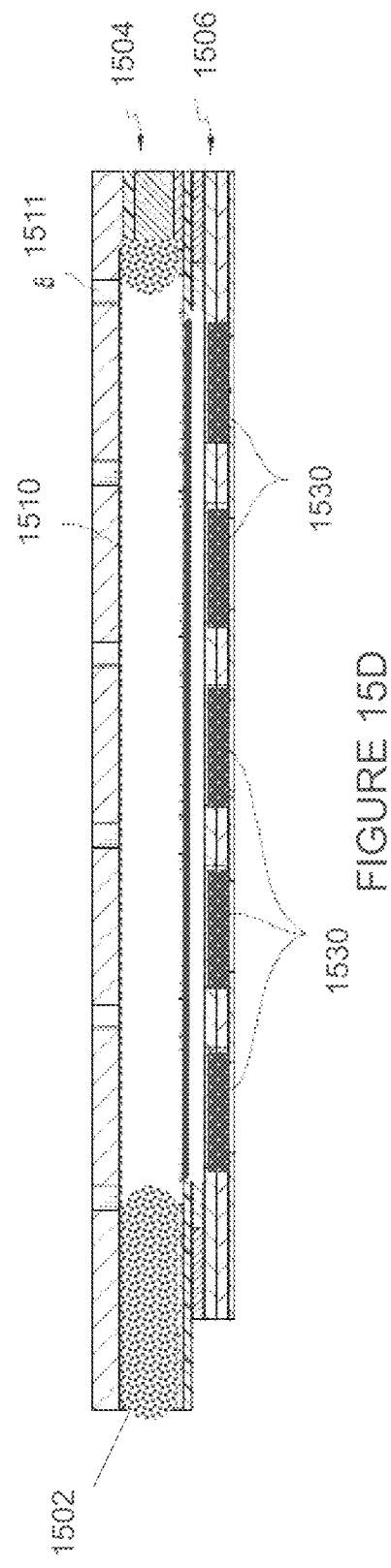

In FIG. 15D, a substantial portion of target analyte 1502 has been drawn out of channel 1510 toward the underlying assay pads 1530 below, resulting in the emptying of a substantial portion of channel 1510. In certain embodiments, portions of the target analyte in the channel above the assay pads "break off" from the target analyte in the rest of the channel, due to the wicking action of the assay pads below. This may result in some target analyte 1502 being left behind in the channel 1510 in regions which are not directly over an assay pad, such as near the ends of the channel, between the end of the channel and the nearest venting hole (see FIG. 15D). Assay pads 1530 receive the portions of the target analyte 1502 that can pass through the separation layer 1531. This portion of the target analyte then undergoes assay reactions in assay pads 1530. In certain embodiments, the assay pads undergo a change (e.g., a color change) which can be detected by the assay reader, as described herein.

Figure 16A:
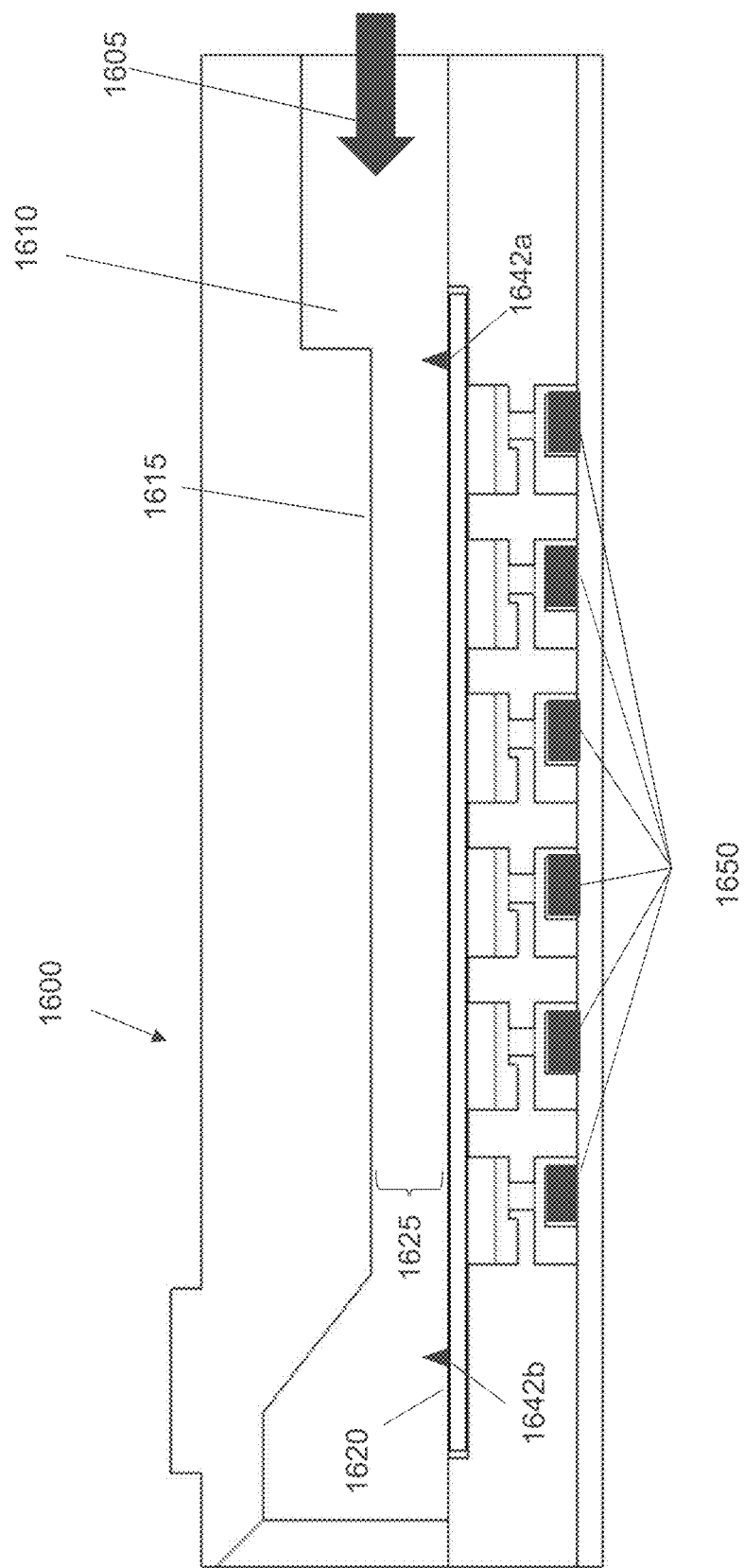
FIG. 16A shows a longitudinal cross sectional view of an assay reader according to one embodiment of the invention.

FIG. 16A shows a schematic drawing of an assay reader, in longitudinal cross-section, according to one non-limiting embodiment of the invention. In FIG. 16A, assay reader 1600 includes cartridge receiving chamber 1610 which houses the cartridge when it is inserted as indicated by arrow 1605. Tab 1615 runs longitudinally along assay reader 1600 and extends into cartridge receiving chamber 1610. Tab 1615 is configured to insert into a slot at the top of the cartridge, such as slot 228 in FIG. 2C or slot 1015 in FIG. 10, when the cartridge is inserted into the assay reader. In addition, the spacing 1625 between the bottom edge of tab 1615 and support surface 1620 is set such that when the cartridge is inserted, tab 1615 compresses the metering stack and the assay stack together, thereby causing the target analyte to flow from the metering stack into the assay stack and initiating the assay reactions. In certain embodiments, the assay reader may comprise a snap-fit mechanism that locks the cartridge in place once it has been fully inserted into the assay reader. This is advantageous because it prevents the user from accidentally removing the cartridge from the assay reader before the assays are complete, which could adversely affect the accuracy of the assay results. In some embodiments, assay reader 1600 also comprises sensors 1642a and 1642b, which detect and time the insertion of the cartridge. For example, as the cartridge is inserted into cartridge receiving chamber 1610 and begins to engage with tab 1615, the bottom surface of the cartridge may pass over sensor 1642a, which is detected by appropriate electronics as the beginning of the insertion of the cartridge. The second sensor, 1642b, is located further inside the assay reader 1600 and detects the presence of the cartridge when the cartridge is fully inserted as well as the time at which full insertion occurred. Assay reader 1600 may then compare the overall time for insertion of the cartridge to determine if the insertion of the cartridge was timely and proper. In this way, assay reader will not perform any assay readings in situations where (1) the cartridge was only partially inserted, or (2) the cartridge was partially inserted, removed, and inserted again. Either case could give inaccurate assay readings, due to incomplete compression of the metering stack and assay stack, resulting in incomplete delivery of the required amount of target analyte to the assay pads in the assay stack.

Figure 16B:
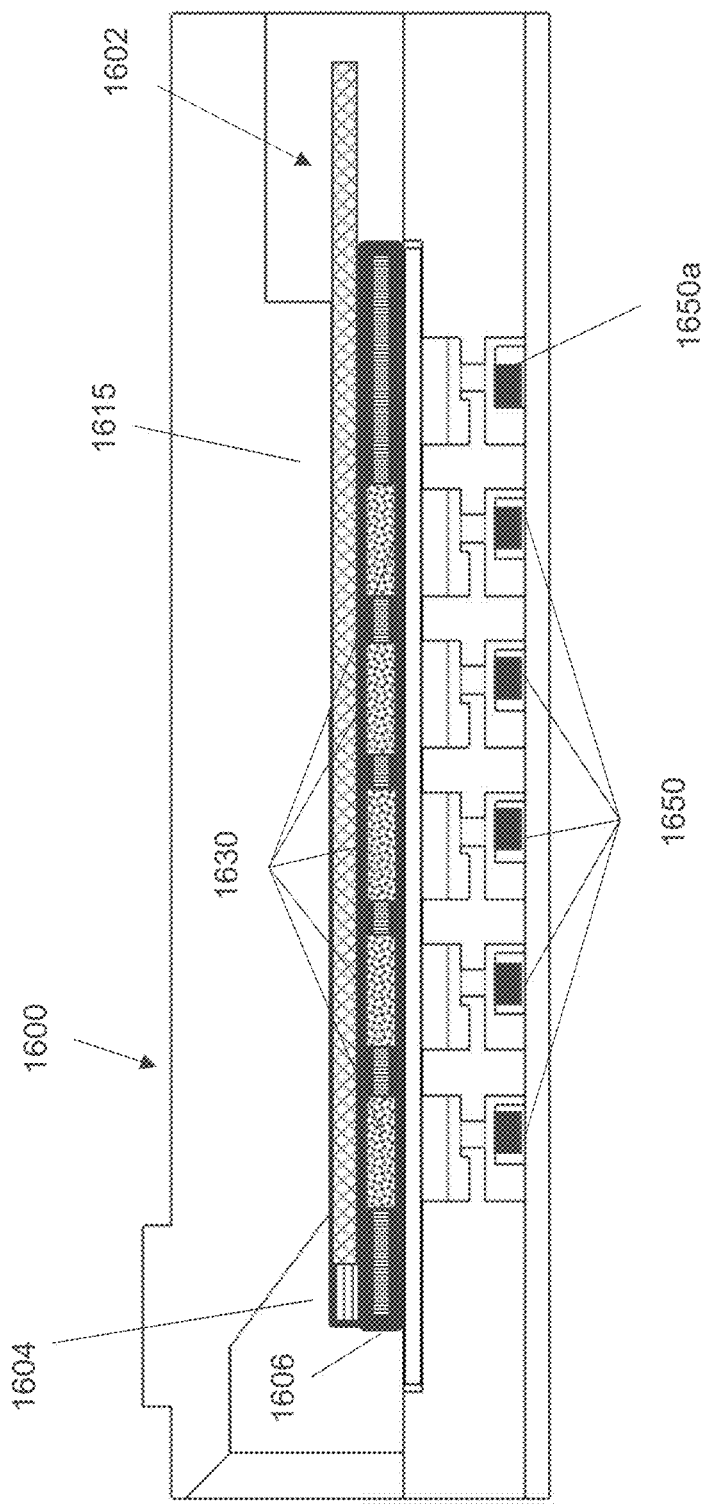
FIG. 16B shows a longitudinal cross sectional view of an assay reader with an inserted cartridge according to one embodiment of the invention.

In the exemplary embodiment shown in FIG. 16A, assay reader 1600 detects the results of the assay by detecting the color change of the assay pad caused by the assay reactions. To achieve this, assay reader 1600 comprises a plurality of light sources (not shown in this cross-sectional drawing) and light detection elements 1650 arrayed within assay reader 1600 such that they align with the assay pads of the cartridge when the cartridge is fully inserted. In order for light detection elements 1650 to be able to detect the color of the assay pads, support surface 1650 may be equipped with one or more apertures or be fabricated from a transparent material that allows light to penetrate therethrough. FIG. 16B shows a schematic illustration of a longitudinal cross-section of assay reader 1600 with cartridge 1602 fully inserted. Cartridge 1602 includes metering stack 1604 and assay stack 1606, which are compressed together by tab 1615 such that the target analyte is delivered from the metering stack 1604 to the assay pads 1630. Assay pads 1630 are aligned with light detection elements 1650. Note, however, that assay reader 1600 may comprise an additional light detection element 1650a without a corresponding assay pad 1630. The presence of additional light detection elements, such as light detection element 1650a, allow the assay reader to be used with different types of cartridges for different assays, particularly cartridges that may be designed to perform more assays, as well as to identify the different types of cartridges for the different assays.

Figure 17A:
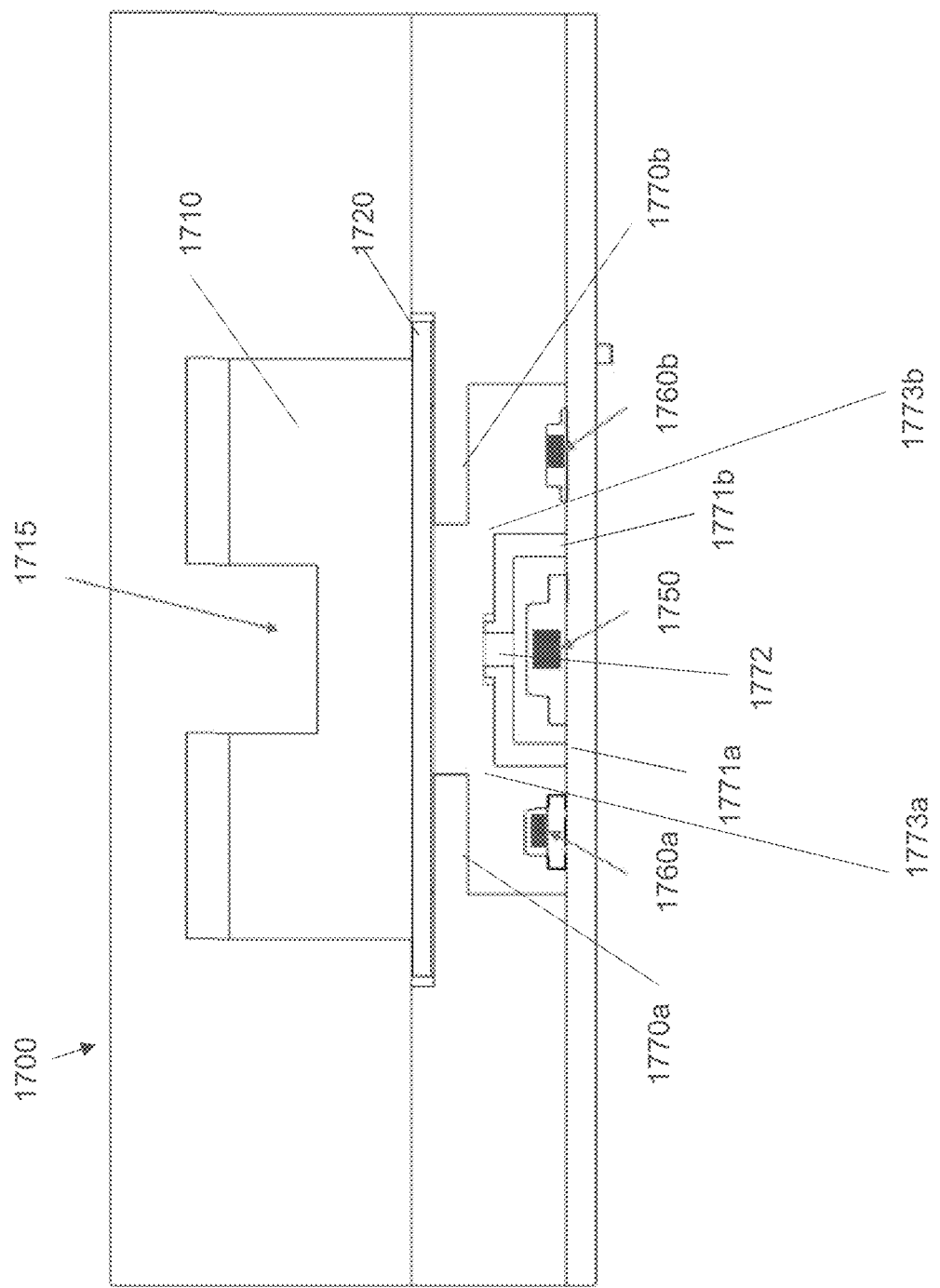
FIG. 17A shows a transverse cross-sectional view of a reader according to one embodiment of the invention.

FIG. 17A shows a schematic drawing of a transverse cross-section of the assay reader shown in FIG. 16. In FIG. 17A, assay reader 1700 includes a tab 1715 that extends into cartridge receiving chamber 1710 to engage with a slot on the cartridge to compress the metering stack and the assay stack against support surface 1720 to initiate the assay reactions. Light sources 1760a and 1760b provide light for detecting the assay results and are positioned near light detection device 1750. As illustrated in FIG. 17A, light sources 1760a and 1760b provide light to analyze the assay pad corresponding to light detection element 1750. In general, it is advantageous to dedicate one or more light sources to each light detection element in order to ensure that the photon flux onto the light detection element is sufficient to obtain an accurate reading. In some embodiments, the light sources dedicated to a particular light detection element have the same output spectrum. In other embodiments, however, the light sources corresponding to a given light detection element produce different output spectra. For instance, the light sources may be light emitting diodes (LEDs) that produce different colors of light. For example, when the target analyte is blood, it may be useful to use light sources that can generate bichromatic pairs (600 nm/570 nm) to detect the presence of undesirable hemolysis. In general, it is advantageous to include optical elements to direct the light and/or reduce the amount of light scattering in the assay reader. In some embodiments, the optical elements are apertures that only allow light emanating from the light source that is line-of-sight to the respective assay pad to reach the assay pad. For example, in FIG. 17A, light source 1760a is limited by aperture defining members 1770a and 1771a such that only the light from light source 1760a that passes through aperture 1773a will reach the assay pad and subsequently be detected by light detection device 1750. Similarly, light source 1760b is limited by aperture defining members 1770b and 1771b, such that only the light from light source 1760b that passes through aperture 1773b will reach the assay pad and subsequently be detected by light detection device 1750. In preferred embodiments, aperture defining members 1770a, 1770b, 1771a, and 1771b are fabricated from a black matte material to reduce the amount of undesirable scattering when light sources 1760a and 1760b are turned on. Furthermore, in this embodiment, light detection device 1750 located in a housing that is comprised of aperture defining members 1771a and 1771b that only permit light that passes through aperture 1772 to reach light detection device 1750. If desired, the aperture 1772 may be fitted with a filter to admit only light of a predetermined wavelength or wavelength range for detection by light detection device 1750. This may be useful, for example, when the light sources are equipped to provide only white light for colorimetric analysis. In addition the light from light sources 1760a and 1760b and the light to be detected by light detection device 1750 may be directed or manipulated using optical elements such as lenses, filters, shutters, fiber optics, light guides, and the like without departing from the spirit and the scope of the invention.

Figure 17B:
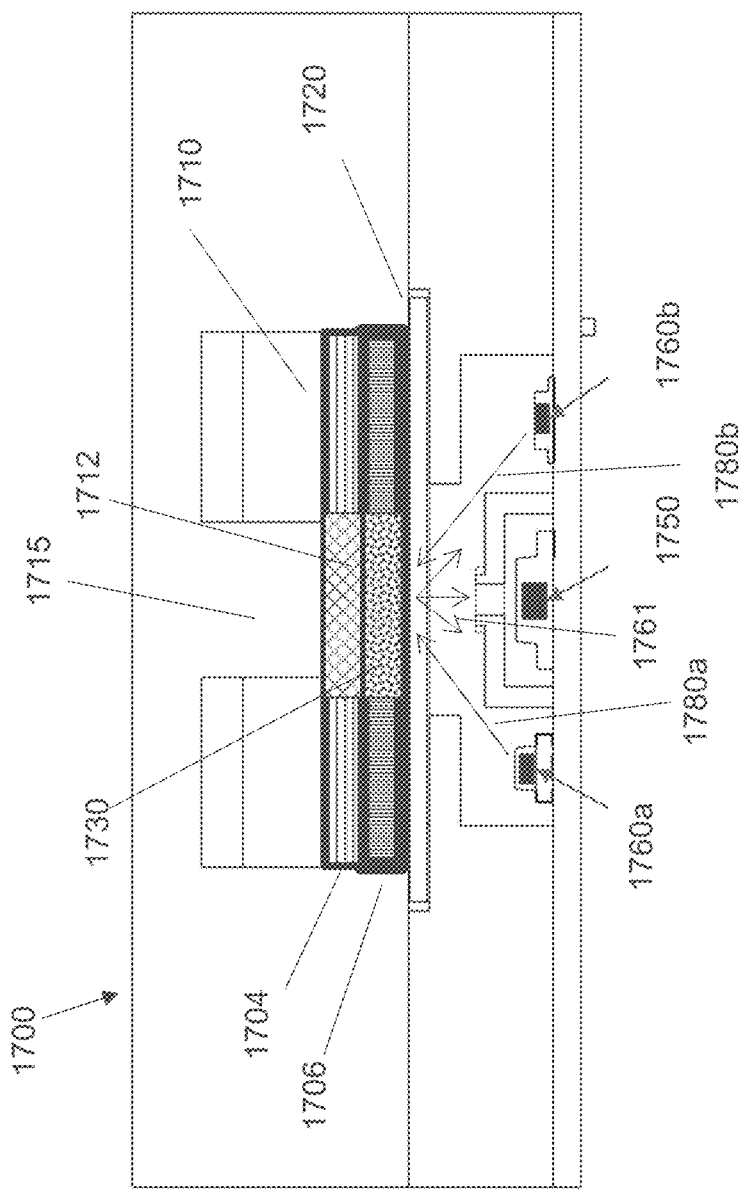
FIG. 17B shows a transverse cross sectional view of an assay reader with an inserted cartridge according to one embodiment of the invention.

FIG. 17B shows a schematic illustration of the operation of the assay reader described in FIG. 17A. In FIG. 17B, a cartridge comprising metering stack 1704 and assay stack 1706 are inserted into cartridge receiving chamber 1710 of assay reader 1700. Tab 1715 compresses metering stack 1704 and assay stack 1706 against support surface 1720 to cause the target analyte to flow from the channel 1712 into assay pad 1730. As noted previously, assay reader 1700 may be fitted with sensors to confirm that the cartridge has been inserted correctly and in a timely manner. Assay reader 1700 may also be pre-programmed before sample collection, either by the user or during the manufacturing process, to illuminate the assay pads at the appropriate time based on the type of cartridge being used. In this way, assay reader 1700 collects assay data from assay pad 1730 only when the assay is completed. Alternatively, if desired, assay reader 1700 may be configured to collect assay data from assay pad 1730 during the entire assay reaction after the cartridge has been inserted. As shown in FIG. 17B, light source 1760a provides light beam 1780a, which impinges on the bottom face of assay pad 1730. Similarly, light source 1760b produces light beam 1780b, which may impinge on the bottom of the assay pad 1730 at the same time as light beam 1760a or a different time, depending on the requirements of the assays being detected.

Figure 18:
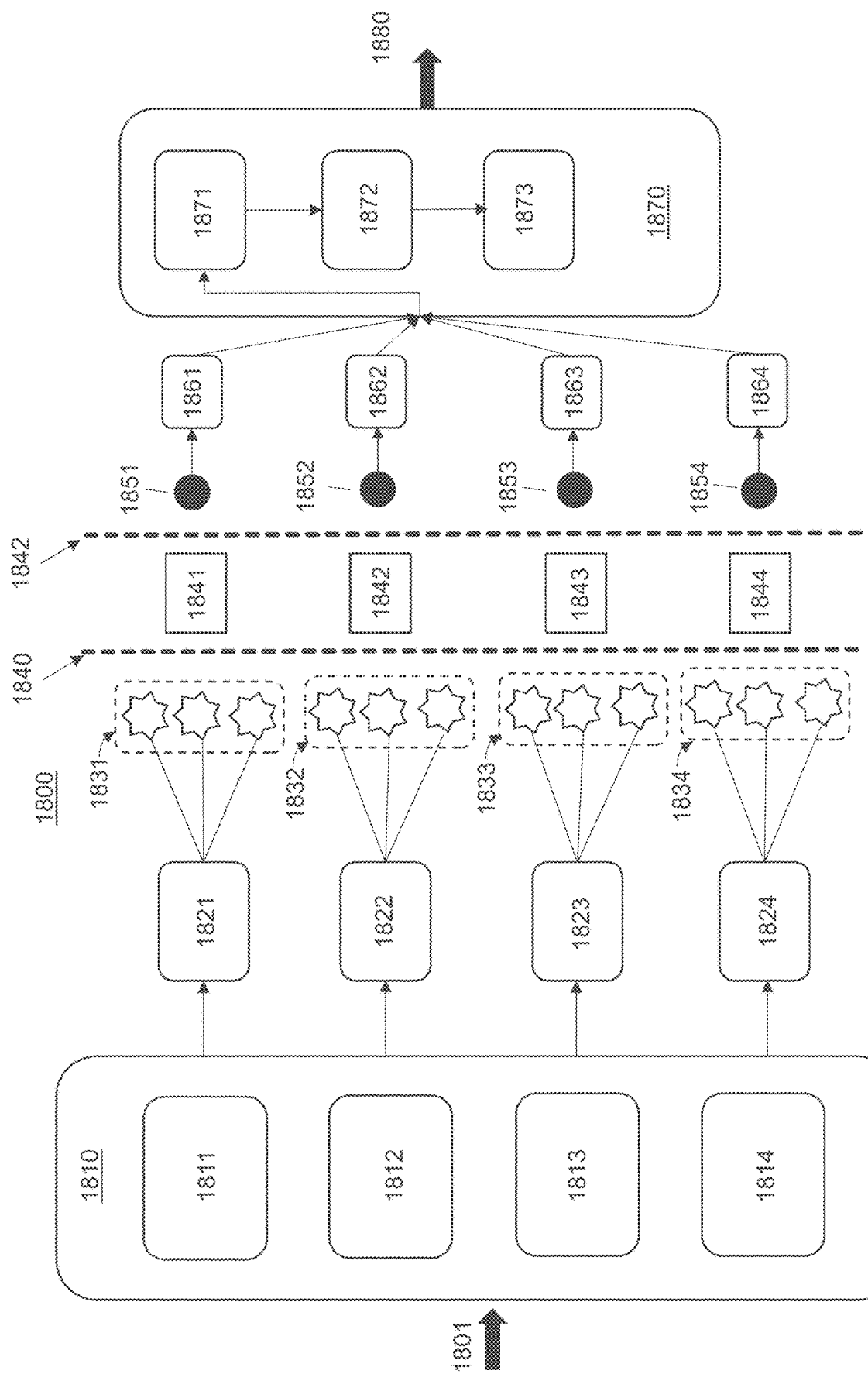
FIG. 18 shows a block diagram of the sensor system of assay reader, according to an exemplary implementation of the invention.

FIG. 18 shows a block diagram of a sensor configuration inside an assay reader according to one exemplary embodiment of the invention. In FIG. 18, four assay pads (identified by reference numerals 1841, 1842, 1843, and 1844) have completed their assay reactions with the target analyte, undergone the respective color changes, and are ready for colorimetric analysis. Note that, if desired, this configuration can also be used to collect data from the four assay pads to monitor the progress of the assay reactions. Input signal 1801 from a first microcontroller serial-peripheral interface bus (MCU SPI Bus) enters digital-to-analog converter unit 1810, which comprises individual digital-to-analog converters 1811, 1812, 1813, and 1814 that independently control current sources 1821, 1822, 1823, and 1824. These current sources, in turn, power light sources 1831, 1832, 1833, and 1834 respectively. In some embodiments, input signal 1801 may be sent by a timing circuit at a predetermined time after the insertion of the cartridge into the assay reader. In such embodiments, the predetermined time corresponds to the known time or times for the assay reactions in the assay pads to reach completion. In some preferred embodiments, the light sources 1831, 1832, 1833, and 1834 are activated at the same time to measure the assay-induced color change of assay pads 1841, 1842, 1843, and 1844 simultaneously in a multiplexed mode. However, this invention also contemplates operating all of the light sources separately and sequentially, or some simultaneously and some separately, depending on the timing requirements of the assays in the cartridge.

In this non-limiting example, each of light sources 1831, 1832, 1833, and 1834 comprises individual three light emitting diodes (LEDs) which may be the same or different colors, depending on the requirements of the assay and any optical elements that may be present in the assay reader. For example, in certain embodiments, the three LEDs in a particular light source (e.g., 1831) may be red, green and blue (RGB LEDs), such that the light impinging on the assay pad is white light when all three LEDS are activated. Of course, the light sources are not limited to any particular number or type of LEDs or other light generating devices. More generally, the light sources that are useful in the assay readers of the invention are not particularly limited, so long as they provide light of suitable wavelength(s) and brightness for the light detection element to make an accurate reading of the colored light reflected from the assay pad. In certain non-limiting embodiments, the light sources are light emitting diodes (LEDs), organic light emitting diodes (OLEDs), active matrix organic light emitting diodes (AMOLEDs) or lasers. For example, the light source may be only one LED that has sufficient brightness and the proper wavelength to allow colorimetric analysis of an assay reaction in a given assay pad. In certain embodiments, the light sources may produce light of specific wavelengths. As one non-limiting example, when the target analyte is blood (with erythrocytes removed), a bichromatic light source that produces light at 570 nm and 600 nm may be used to detect the presence of heme on a non-functional (i.e., assay reagent-free) assay pad, which is indicative of undesirable hemolysis in the patient. Alternatively, the light source may be a broadband source that is paired with one or more narrow bandpass filters to select light of certain desired wavelength(s). Typically, the light sources produce light in the visible region of the electromagnetic spectrum (i.e., wavelength between 400-700 nm) although this invention also contemplates light sources that produce electromagnetic radiation in the infrared (700 nm to $10^6$ nm) or ultraviolet regions (10 nm-400 nm) of the electromagnetic spectrum, so long as they are paired with the appropriate light detection devices. Combinations of different light sources are also expressly contemplated by the invention.

In FIG. 18, element 1840 is a schematic representation of optical elements that optionally may be present in the optical path between the light sources 1831, 1832, 1833, and 1834 and assay pads 1841, 1842, 1843, and 1844. When desired, one or more optical elements may be located between the light source and its corresponding assay pad to direct the light, focus the light, reduce undesirable scattering, select one or more wavelengths for assay detection, or some combination thereof. Non-limiting examples of such optical elements include apertures, lenses, light guides, bandpass filters, optical fibers, shutters, and the like. Similarly, element 1842 represents optical elements that optionally may be present in the optical path between assay pads 1841, 1842, 1843, and 1844 and corresponding light detection devices 1851, 1852, 1853, and 1854. These optical elements may be used to manipulate the light upstream of the light detector devices in a manner similar to that described for element 1840. It is to be understood that different types and numbers of optical elements may be used for each combination of light source, assay pad, and light detection device. Light detecting devices 1851, 1852, 1853, and 1854 detect the light from the assay pads 1841, 1842, 1843, and 1844. In this non-limiting example, the light detecting devices are photodiodes. More generally, the type of light detection device is not particularly limited, provided that it is capable of detecting the light that is reflected from the assay pads used for colorimetric measurement of the assay results. Other examples of suitable light detection elements include photodiode arrays, CCD chips, and CMOS chips. The outputs from photodiodes 1851, 1852, 1853, and 1854 are sent to transimpedance amplifier/low pass filter elements 1861, 1862, 1863, and 1864, which convert the current signal from the photodiodes to a voltage output, while filtering unwanted signal components. The output from elements 1861, 1862, 1863, and 1864 are sent to analog-to-digital converter unit 1870, which comprises multiplexer unit 1871, gain 1872, and analog-to-digital converter 1873. The output of analog-to-digital converter unit 1870 may be sent to a component 1880, which may be a second MCU SPI bus, a transmitter, or a processor. In certain embodiments, the transmitter allows for hardwired or wireless connectivity (e.g., Bluetooth or Wi-Fi) with a personal computer, mobile device, or computer network. In one particularly useful embodiment, the assay results are transmitted to the user's mobile device or personal computer, where they are displayed in a graphical user interface (GUI). If desired, the GUI may display prior assay results, in addition to the current results, in order to provide the user with information regarding the overall trends in the results of the assays. For example, if the user is diabetic, the GUI may plot the glucose levels measured by the assay reader as a function of time to allow the user to determine whether blood glucose level is being properly controlled. In addition, the assay results may be transmitted from the user's mobile device or computer to a computer network, such as one belonging to the user's physician. In this way, the assay systems of the invention can allow a user's physician to monitor a patient closely, by providing up-to-date medical information from the assay results obtained by the assay reader.

It should be noted that the optical detection systems described in the foregoing correspond to some exemplary embodiments of the system, but that the invention expressly contemplates other types of detection systems as well. In general, any detection system which corresponds to a signal change caused by an assay reaction may be used in connection with the assay reader of the invention. Thus, for example, in certain embodiments, the detection system is an optical detection system that is based on chemiluminescence. In such embodiments, light sources such as LEDS and OLEDS are not required to detect a color change caused by the assay reaction in the assay pads. Rather, the signal change may be caused by the reaction of an oxidative enzyme, such as luciferase, with a substrate which results in light being generated by a bioluminescent reaction. In another exemplary embodiment, the signal change caused by the assay reaction may be detected by electrochemical reaction. As one non-limiting example, the presence of glucose in a biological sample may be tested using an electrochemical enzymatic sensor, which consists of a platinum electrode coated with a glucose oxidase layer that is separated from the biological sample by a semipermeable membrane. Such sensors have been reported, for example, by Mor et al., in an article entitled "Assay of glucose using an electrochemical enzymatic sensor" Analytic Biochemistry, Vol. 79, Issues 1-2, May 1977 pp. 319-328, which is hereby incorporated by reference in its entirety.

Figure 19:
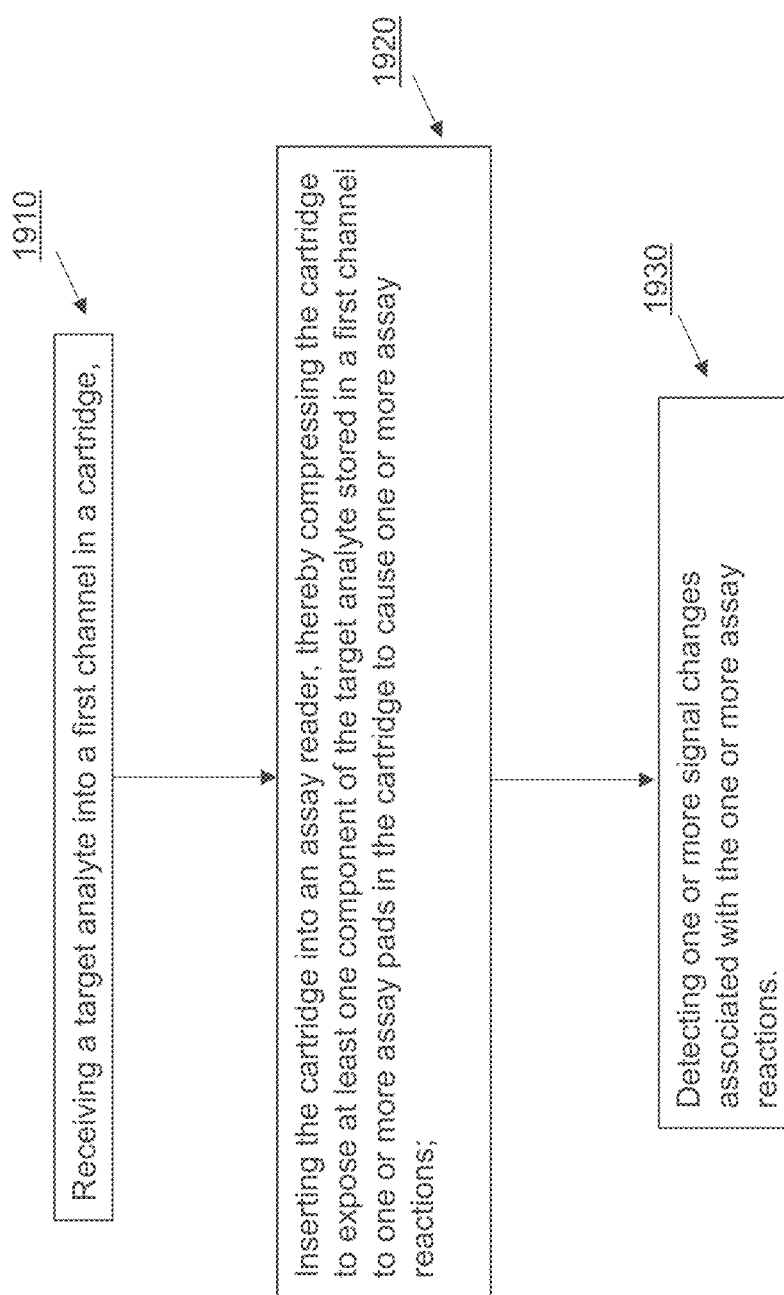
FIG. 19 shows a flow chart illustrating a method of using the assay system according to an exemplary implementation of the invention.

FIG. 19 shows a flowchart that illustrates a method of using of the assay system according to one embodiment of the invention to perform a plurality of assays. The method includes step 1910, which involves receiving a target analyte into a first channel in a cartridge. Step 1920 involves inserting the cartridge into an assay reader, thereby compressing the cartridge to expose at least one component of the target analyte stored in a first channel to a plurality of assay pads in the cartridge simultaneously to cause a plurality of assay reactions. Step 1930 involves detecting one or more signal changes associated with the plurality of assay reactions.

Figure 20:
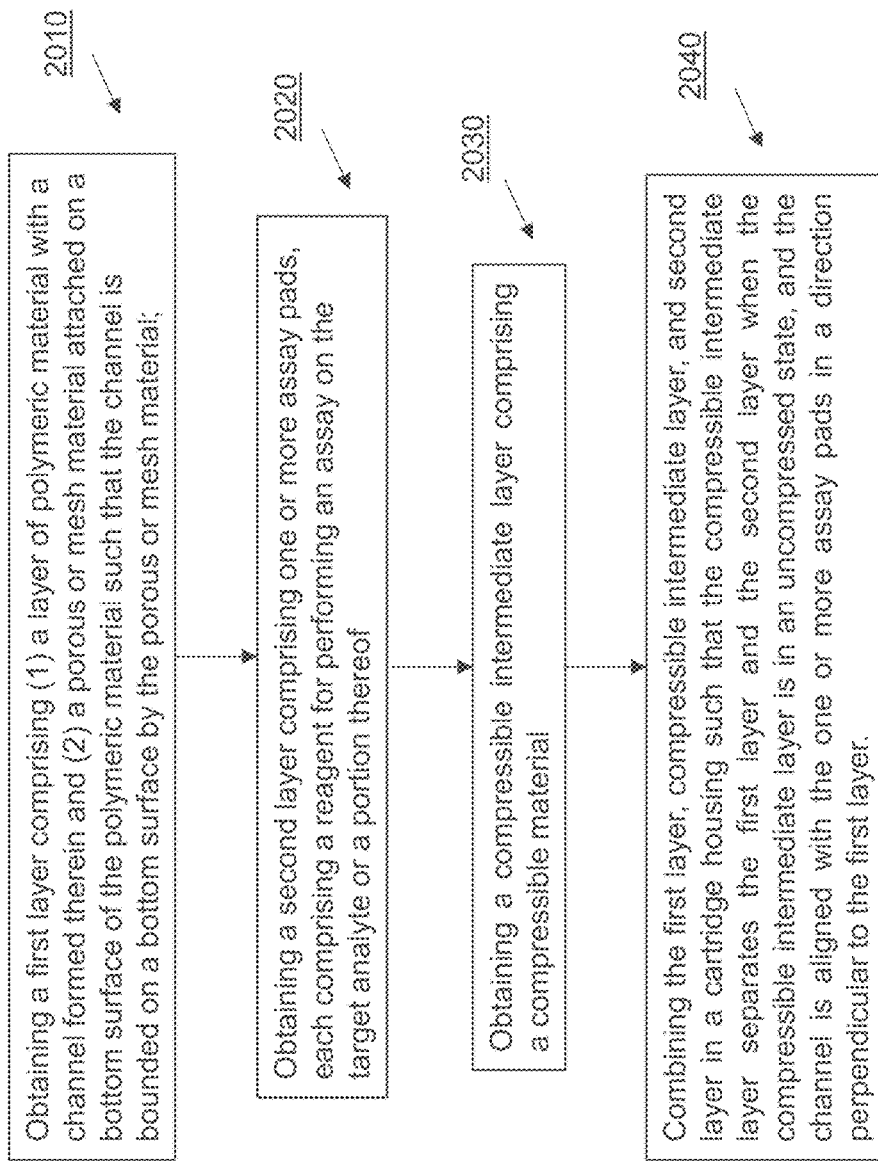
FIG. 20 shows a flow chart illustrating a method of manufacturing a cartridge according to one exemplary implementation of the invention.

FIG. 20 shows a flowchart that illustrates a method of fabricating a cartridge according to one embodiment of the invention. The method includes the steps of obtaining a first layer comprising (1) a layer of polymeric material with a channel formed therein and (2) a porous or mesh material attached on a bottom surface of the polymeric material such that the channel is bounded on a bottom surface by the porous or mesh material; (step 2010) and obtaining a second layer comprising two or more assay pads, each comprising a reagent for performing an assay on the target analyte or a portion thereof (step 2020). The method also includes the step of obtaining a compressible intermediate layer comprising a compressible material (step 2030). It is to be understood that steps 2010, 2020, and 2030 can occur independently, and not necessarily stepwise or sequentially. In addition, in certain embodiments, the compressible intermediate layer can be attached to, or be a part of the first or second layer. The method also includes the step of combining the first layer, compressible intermediate layer, and second layer in a cartridge housing such that the compressible intermediate layer separates the first layer and the second layer when the compressible intermediate layer is in an uncompressed state, and the channel is aligned with the two or more assay pads in a direction perpendicular to the first layer (step 2040).

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A system for multiplexed analysis of a target analyte, the system comprising:
a cartridge, wherein the cartridge comprises:
a metering stack configured to receive and distribute the target analyte along a first channel, wherein the first channel has a bottom that comprises a porous or mesh material;
an assay stack comprising at least one assay component, each assay component comprising one or more assay pads for performing an assay on the target analyte or a portion thereof; and
a spacing mechanism providing a separation between the metering stack and the assay stack that prevents the target analyte from flowing from the metering stack into the assay stack only when the cartridge is in an uncompressed state, the porous or mesh material of the first channel permitting the target analyte to flow from the metering stack to the assay stack upon the metering stack coming into contact with the assay stack, and
an assay reader, wherein the assay reader comprises:
a region configured to receive the cartridge;
a compression mechanism configured to bring the assay stack and metering stack into contact when or after the cartridge is inserted into the region after collection of the target analyte, thereby causing two or more assay reactions to start within the cartridge; and
a detection system for detecting a signal change caused by the two or more assay reactions.

2. The system according to claim 1, wherein the detection system is an optical system that comprises at least one light source and at least one light detection device for colorimetric measurement of assay results corresponding to the one or more assay reactions.

3. The system according to claim 1, wherein the detection system comprises an optical detection system comprising at least one light detection device for detecting a chemiluminescent signal caused by the one or more assay reactions.

4. The system according to claim 1, wherein the detection system comprises an electrochemical detection system that detect electrochemical signal change caused by the one or more assay reactions.

5. The system according to claim 1, wherein the target analyte comprises a biological fluid selected from the group consisting of blood, serum, plasma, saliva, sweat, urine, lymph, tears, synovial fluid, breast milk, and bile, or a component thereof.

6. The system according to claim 5, wherein the target analyte is blood and the assay stack comprises a separation layer that prevents erythrocytes from contacting the one or more assay pads.

7. The system according to claim 1, wherein the first channel further comprises a plurality of receiving chambers, each configured to deliver a predetermined volume of the target analyte to the assay stack only when the cartridge is sufficiently compressed to bring the metering stack in contact with the assay stack.

8. The system according to claim 1, wherein the first channel further comprises a plurality of venting holes along the first channel.

9. The system according to claim 1, wherein the first channel is in fluid communication with a reservoir that is adapted to receive the target analyte.

10. The multiplexed system according to claim 1, wherein the cartridge further comprises a second channel in fluid communication with the first channel along a length of the first channel.

11. The system according to claim 10, wherein the second channel comprises a receiving chamber in fluid communication with a corresponding receiving chamber of the first channel.

12. The system according to claim 11, wherein the receiving chamber of the second channel has a larger volume than the corresponding receiving chamber of the first channel.

13. The system according to claim 1, wherein the first channel splits into a plurality of second channels.

14. A method of performing a plurality of assays, the method comprising
receiving a target analyte into a first channel in a cartridge,
inserting the cartridge into an assay reader, thereby compressing the cartridge to expose at least one component of the target analyte stored in a first channel to a plurality of assay pads in the cartridge simultaneously to cause a plurality of assay reactions;
detecting one or more signal changes associated with the plurality of assay reactions.

15. The method according to claim 14, wherein the target analyte comprises blood and the cartridge comprises a separation layer to prevent erythrocytes in the blood from contacting the plurality of assay pads.

16. The method according to claim 14, wherein the first channel comprises a plurality of receiving chambers arranged along the channel.

17. The method according to claim 16, wherein each of the plurality of receiving chambers is configured to deliver a predetermined volume of at least one component of the target analyte to one of the plurality of assay pads.

18. The method according to claim 14, wherein the first channel further comprises a plurality of venting holes along the first channel.

19. An analyte analysis system, the system comprising:
a cartridge, wherein the cartridge comprises:
a metering stack comprising a first channel, wherein the first channel comprises a porous or mesh material and one or more venting holes;
an assay stack comprising one or more assay pads, at least one of the assay pads comprising a reagent for performing an assay; and
a spacing mechanism positioning the metering stack and the assay stack apart from each other only when in an uncompressed state and allowing the metering stack and the assay stack to come into contact when in a compressed state, wherein the porous or mesh material permits flow from the metering stack to the assay stack when in the compressed state;
an assay reader, wherein the assay reader comprises a chamber configured to receive the cartridge;
a compression mechanism configured to compress the cartridge when or after the cartridge is inserted into the chamber after collection of the target analyte, thereby causing two or more assay reactions to start within the cartridge; and
a detection system for detecting a signal change caused by the two or more assay reactions.

20. The system according to claim 18, wherein the detection system comprises an optical system, an electrochemical system, or both.

* * * * *